US012617819B2

(12) United States Patent
Choi et al.

(10) Patent No.: US 12,617,819 B2
(45) Date of Patent: May 5, 2026

(54) INTERMEDIATE USED FOR BIOLOGICALLY ACTIVE POLYPEPTIDE AND METHOD FOR PREPARING SAME

(71) Applicant: HANMI FINE CHEMICAL CO., LTD., Siheung-si (KR)

(72) Inventors: Wonkyoung Choi, Siheung-si (KR); Nari Kim, Incheon (KR); Jonghwan Park, Siheung-si (KR); Sungjun Park, Seoul (KR); Namdu Kim, Yongin-si (KR); Youngbum Cho, Anyang-si (KR)

(73) Assignee: HANMI FINE CHEMICAL CO., LTD., Siheung-si (KR)

( * ) Notice: Subject to any disclaimer, the term of this patent is extended or adjusted under 35 U.S.C. 154(b) by 240 days.

(21) Appl. No.: 17/430,864

(22) PCT Filed: Feb. 14, 2020

(86) PCT No.: PCT/KR2020/002084

§ 371 (c)(1),
(2) Date: Mar. 24, 2022

(87) PCT Pub. No.: WO2020/167010

PCT Pub. Date: Aug. 20, 2020

(65) Prior Publication Data

US 2022/0242913 A1 Aug. 4, 2022

(30) Foreign Application Priority Data

Feb. 15, 2019 (KR) ........................ 10-2019-0017766

(51) Int. Cl.

| | |
|---|---|
| ***C07K 7/56*** | (2006.01) |
| ***C07K 1/06*** | (2006.01) |
| ***C07K 1/10*** | (2006.01) |
| ***C07K 7/08*** | (2006.01) |
| ***C07K 7/64*** | (2006.01) |
| ***C07K 14/00*** | (2006.01) |

(52) U.S. Cl.

CPC ................ *C07K 7/56* (2013.01); *C07K 1/061* (2013.01); *C07K 1/10* (2013.01); *C07K 7/08* (2013.01); *C07K 7/64* (2013.01); *C07K 14/001* (2013.01)

(58) Field of Classification Search

None

See application file for complete search history.

(56) References Cited

U.S. PATENT DOCUMENTS

| | | | | |
|---|---|---|---|---|
| 7,928,058 B2 | 4/2011 | Sinha Roy et al. | | |
| 2014/0128318 A1* | 5/2014 | Jung | .................... | A61K 38/177<br>514/4.8 |
| 2019/0002520 A1* | 1/2019 | Oh | ..................... | A61K 39/3955 |

FOREIGN PATENT DOCUMENTS

| | | |
|---|---|---|
| KR | 10-2014-0018462 A | 2/2014 |
| KR | 10-2014-0058104 A | 5/2014 |
| KR | 10-2014-0058387 A | 5/2014 |
| KR | 10-2014-0113696 A | 9/2014 |
| KR | 10-2017-0080521 A | 7/2017 |

OTHER PUBLICATIONS

International Search Report for PCT/KR2020/002084 dated May 26, 2020 (PCT/ISA/210).

* cited by examiner

*Primary Examiner* — Christina Bradley
(74) *Attorney, Agent, or Firm* — Sughrue Mion, PLLC

(57) ABSTRACT

The present invention relates to a novel intermediate used for physiologically active polypeptides and a method for preparing the same. The novel intermediate may be effectively used as an intermediate for the preparation of physiologically active polypeptide pharmaceuticals, and may be efficiently used for the preparation of high-quality pharmaceuticals by providing a polypeptide intermediate of high yield and high purity.

17 Claims, 1 Drawing Sheet

Specification includes a Sequence Listing.

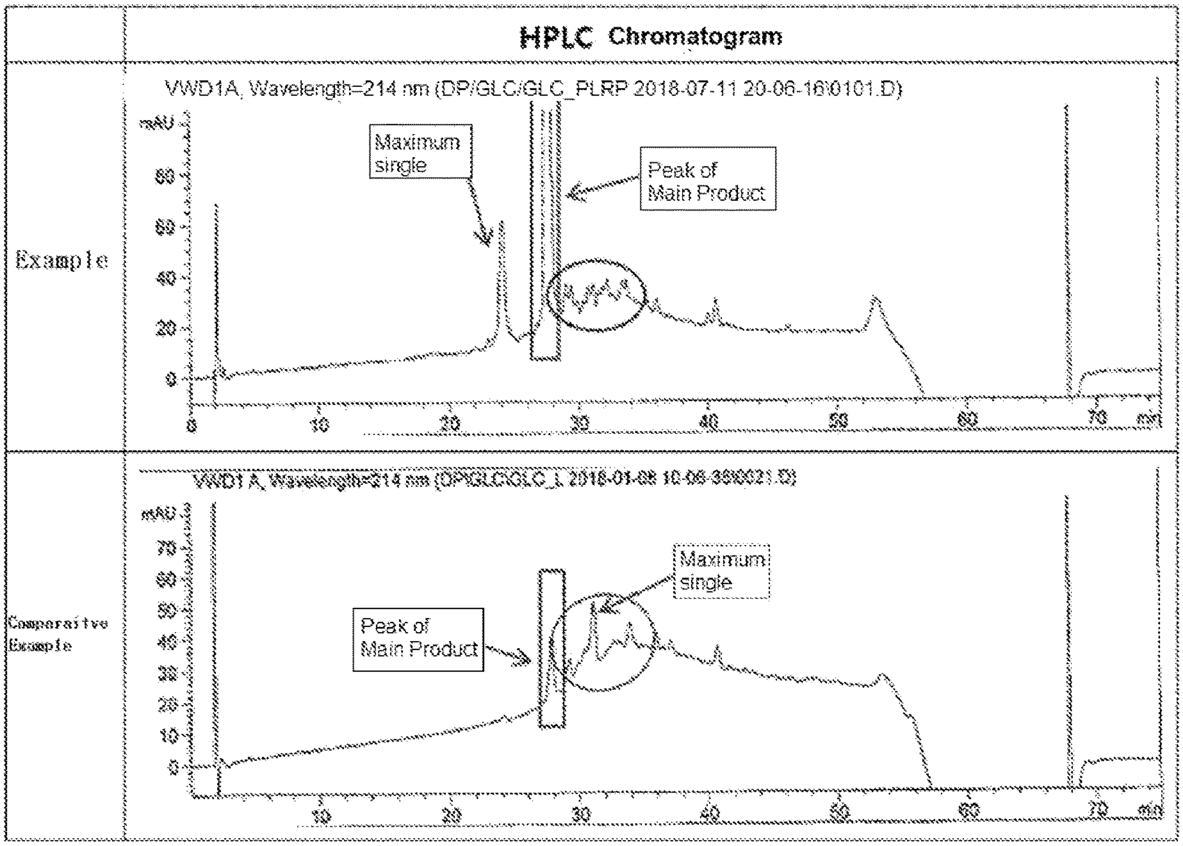
HPLC Chromatogram
Example
VWD1A, Wavelength=214 nm (DP/GLC/GLC_PLRP 2018-07-11 20-06-16\0101.D)
mAU
Maximum single
Peak of Main Product
min
Comparaitve Example
mAU
Peak of Main Product
Maximum single
min

INTERMEDIATE USED FOR BIOLOGICALLY ACTIVE POLYPEPTIDE AND METHOD FOR PREPARING SAME

CROSS REFERENCE TO RELATED APPLICATIONS

This application is a National Stage of International Application No. PCT/KR2020/002084 filed Feb. 14, 2020, claiming priority based on Korean Patent Application No. 10-2019-0017766 filed Feb. 15, 2019.

INCORPORATION BY REFERENCE OF SEQUENCE LISTING

The content of the electronically submitted sequence listing, file name: Q266743 SEQ_ST25.txt; size: 60,254 bytes; and date of creation: Sep. 15, 2025, filed herewith, is incorporated herein by reference in its entirety.

TECHNICAL FIELD

The present invention relates to a novel intermediate used for physiologically active polypeptides and a method for preparing the same. More specifically, the present invention relates to a method for preparing a physiologically active polypeptide in a safer and more effective manner, a novel polypeptide intermediate used therefor, and a method for preparing the same.

BACKGROUND ART

Diabetes-related diseases, including obesity and type 2 diabetes, are among the typical metabolic diseases developing in modern society, and are recognized as an important threat to health worldwide. Accordingly, economic costs are also increasing rapidly.

Research has been conducted on the development of pharmaceuticals that can be used for the treatment of obesity and diabetes, but these have the disadvantages of showing fatal side effects or having insignificant effects on the treatment of obesity. Therefore, research that can solve the problems arising with conventional therapeutics is actively underway, and recently, much attention has been paid to glucagon derivatives. Glucagon is produced in the pancreas when the blood glucose levels fall due to reasons such as medications, diseases, deficiency in hormones or enzymes, etc. Glucagon sends a signal for glycogen breakdown in the liver to induce the release of glucose and increases blood glucose to a normal level. In addition to the effect of increasing the blood glucose levels, glucagon suppresses appetite and activates hormone-sensitive lipase of adipocytes to promote lipolysis, thereby showing an anti-obesity effect. Various studies related to glucagon are underway.

In one example, Korean Laid-Open Publication No. 10-2017-0080521 discloses a triple agonist having activities to all of glucagon, GLP-1, and GIP receptors and uses thereof. Such a peptide may be composed of substitution, addition, deletion, modification, and combinations thereof in at least one or more amino acids in the native glucagon sequences, and more specifically, it discloses an isolated peptide including the amino acid sequence represented by the following General Formula 1:

[General Formula 1]

(SEQ ID NO: 49)

Xaa1-Xaa2-Xaa3-Gly-Thr-Phe-Xaa7-Ser-Asp-Xaa10-Ser-Xaa12-Xaa13-Xaa14-Xaa15-Xaa16-Xaa17-Xaa18-Xaa19-Xaa20-Xaa21-Phe-Xaa23-Xaa24-Trp-Leu-Xaa27-Xaa28-Xaa29-Xaa30-R1

(SEQ ID NO: 103 of the KR 10-2017-0080521).

The peptide may be prepared by way of methods known in the art, for example, synthesis via an automatic peptide synthesizer, genetic manipulation technique, or any other methods, depending on the length of the peptide. In order to use the peptides prepared by way of these various production methods as pharmaceuticals, the quality of high purity, a yield suitable for commercialization, and a production process suitable for mass production are required.

Therefore, there is a need for a novel polypeptide intermediate that enables the efficient production of such physiologically active polypeptides and an efficient production method capable of providing the same. Accordingly, the present inventors have completed the present invention by developing a novel polypeptide intermediate and a method for preparing the same, as a result of research on a method for preparing a physiologically active polypeptide more safely and efficiently.

PRIOR ART LITERATURE

Patent Literature

Korean Laid-Open Publication No. 10-2017-0080521 (2017 Jul. 10), Triple agonist having activities to all of glucagon, GLP-1, and GIP receptors

DISCLOSURE

Technical Problem

It is one object of the present invention to provide a novel polypeptide intermediate and a resin composite compound used for physiologically active polypeptides.

It is another object of the present invention to provide a method for efficiently preparing the novel polypeptide intermediate and resin composite compound.

It is still another object of the present invention to provide a method for efficiently preparing a physiologically active polypeptide used for the novel polypeptide intermediate.

Technical Solution

In order to achieve the above objects, one aspect of the present invention provides a novel polypeptide intermediate represented by Chemical Formula 1 below:

[Chemical Formula 1]

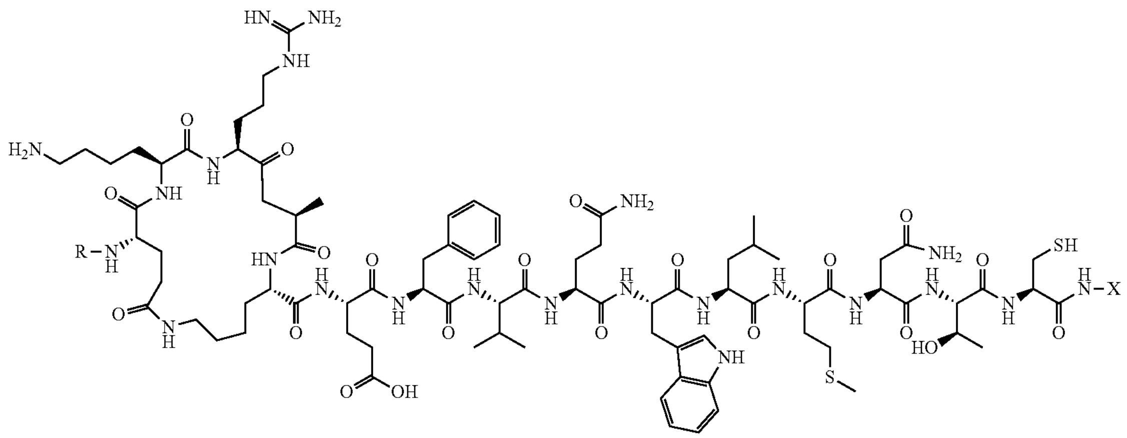

R-cyclo(Glu-Lys-Arg-Ala-Lys)-Glu-Phe-Val-Gln-Trp-Leu-Met-Asn-Thr-Cys-X (SEQ ID NO: 1):

wherein, R is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; X is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; and these substituents may be further substituted with one or more identical or different substituents selected from the group consisting of H, halogen, cyano, linear or branched $C_{1-6}$ alkyl, linear or branched $C_{2-10}$ alkenyl, $C_{3-10}$ cycloalkyl, halo $C_{1-5}$ alkyl, hydroxy $C_{1-6}$ alkyl, amino, mono or di $C_{1-6}$ alkylamino, oxo, hydroxy, $C_{1-6}$ alkoxy, $C_{6-12}$ arylsulfonyl, and $C_{1-6}$ alkylsulfonyl.

Additionally, in one embodiment of the present invention, there is provided a novel resin composite compound represented by Chemical Formula 3 below:

wherein A to D are protecting groups; A to D are each independently selected from the group consisting of triphenylmethyl (Trt), tert-butyl (tBu), t-butyloxycarbonyl (Boc), and 2,2,4,6,7-pentamethyldihydrobenzofuran-5-sulfonyl (Pbf); R is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; X' is a resin; and these substituents may be further substituted with one or more identical or different substituents selected from the group consisting of H, halogen, cyano, linear or branched $C_{1-6}$ alkyl, linear or branched $C_{2-10}$ alkenyl, $C_{3-10}$ cycloalkyl, halo $C_{1-5}$ alkyl, hydroxy $C_{1-6}$ alkyl, amino, mono or di $C_{1-6}$ alkylamino, oxo, hydroxy, $C_{1-6}$ alkoxy, $C_{6-12}$ arylsulfonyl, and $C_{1-6}$ alkylsulfonyl.

Additionally, in one embodiment of the present invention, there is provided a method for preparing a resin composite compound represented by Chemical Formula 3 below, including the steps of:

(1) swelling a resin in a polar aprotic solvent; (2) preparing a deprotected resin by removing the protecting

[Chemical Formula 3]

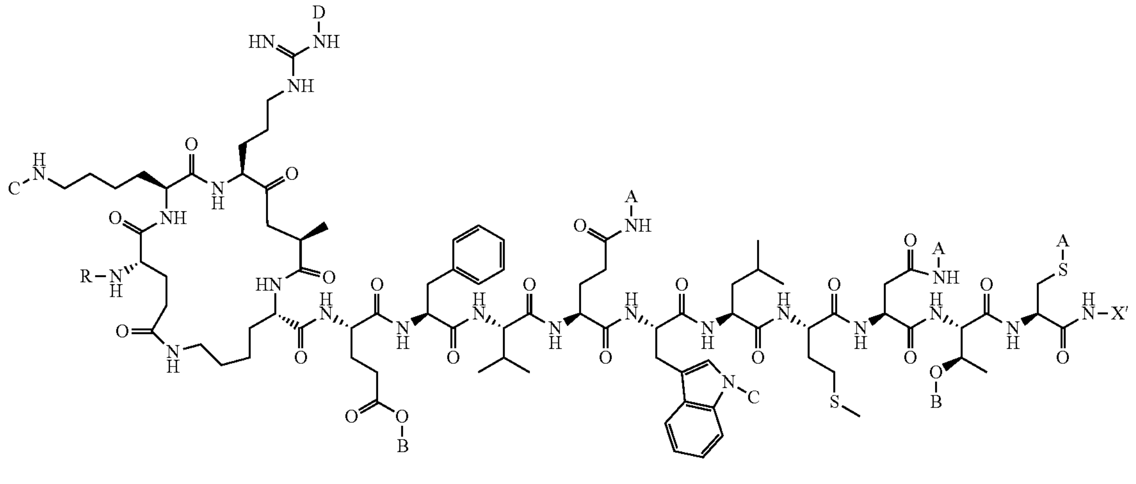

group using a piperidine solution in a polar aprotic solvent; (3) activating the protected amino acid by adding the protected amino acid, 1-hydroxy-1H-benzotriazole, and 1,3-diisopropylcarbodiimide in a polar aprotic solvent; (4) coupling by adding an activated protected amino acid solution to the deprotected resin in a reactor; (5) repeating steps (2)-(4) until a peptide is formed; (6) preparing a partially deprotected resin by reacting the synthesized peptide with tetrakispalladium, N-methylaniline, and phenylsilane in a solvent; and (7) cyclizing the synthesized peptide by adding a coupling reagent in a polar aprotic solvent:

[Chemical Formula 3]

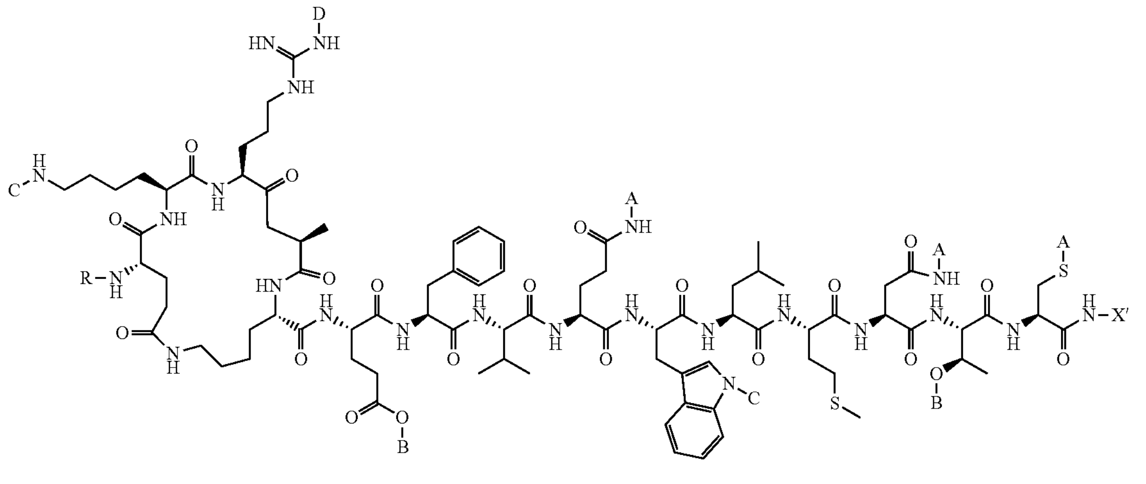

wherein A to D are protecting groups; A to D are each independently selected from the group consisting of triphenylmethyl (Trt), tert-butyl (tBu), t-butyloxycarbonyl (Boc), and 2,2,4,6,7-pentamethyldihydrobenzofuran-5-sulfonyl (Pbf); R is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; X' is a resin; and these substituents may be further substituted with one or more identical or different substituents selected from the group consisting of H, halogen, cyano, linear or branched $C_{1-6}$ alkyl, linear or branched $C_{2-10}$ alkenyl, $C_{3-10}$ cycloalkyl, halo $C_{1-5}$ alkyl, hydroxy $C_{1-6}$ alkyl, amino, mono or di $C_{1-6}$ alkylamino, oxo, hydroxy, $C_{1-6}$ alkoxy, $C_{6-12}$ arylsulfonyl, and $C_{1-6}$ alkylsulfonyl.

Additionally, in one embodiment of the present invention, there is provided a method for preparing a physiologically polypeptide and a pharmaceutically acceptable salt thereof, including the steps of:

(1) preparing a deprotected resin by removing the protecting group of the cyclized peptide compound prepared by way of the above method using a piperidine solution in a polar aprotic solvent; (2) activating the protected amino acid by adding the protected amino acid, 1-hydroxy-1H-benzotriazole, and 1,3-diisopropylcarbodiimide in a polar aprotic solvent; (3) coupling by adding an activated protected amino acid solution to the deprotected resin in a reactor; (4) repeating steps (1)-(3) until a peptide is formed; (5) deprotecting the protected resin using a cleavage cocktail while simultaneously cleaving the desired peptide from the resin; and (6) filtering the cleaved mixture from the resin.

In one embodiment of the present invention, there is provided a method for preparing a physiologically active polypeptide represented by Chemical Formula 2 below and a pharmaceutically acceptable salt thereof:

[Chemical Formula 2]
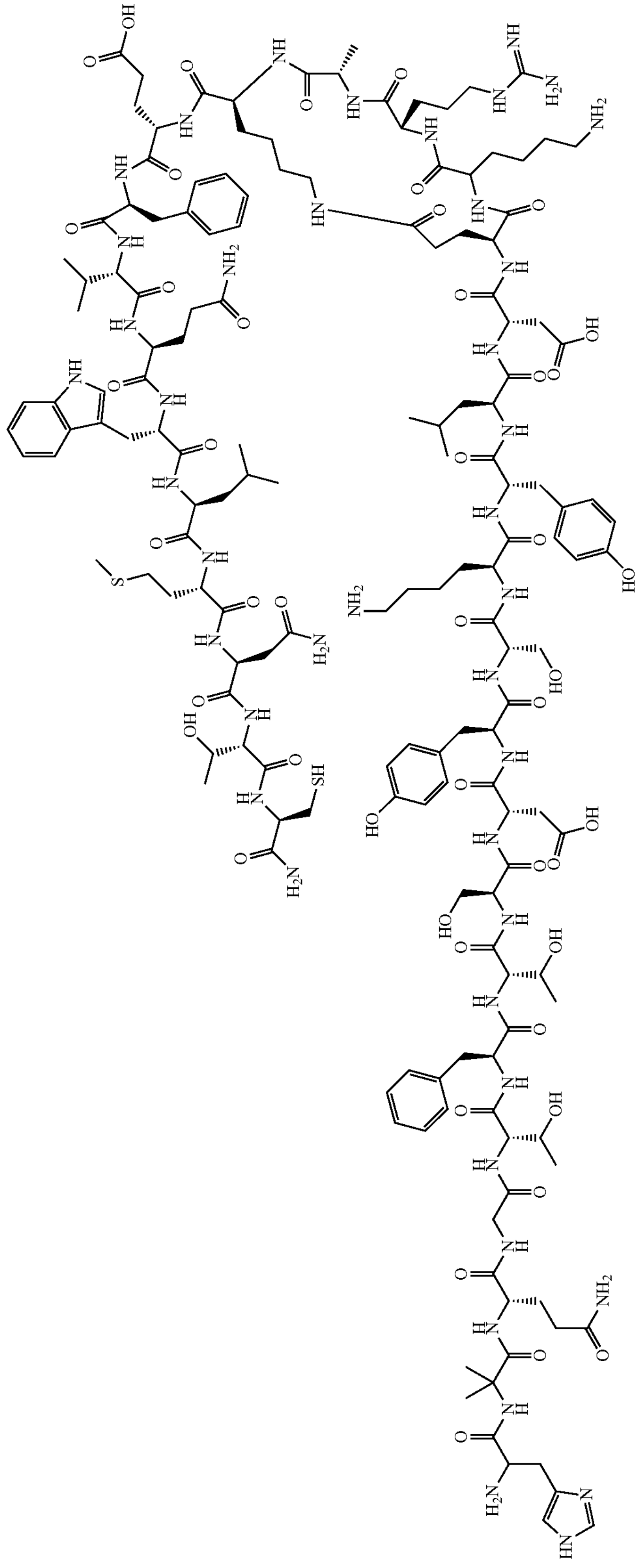

H-His-Aib-Gln-Gly-Thr-Phe-Thr-Ser-Asp-Tyr-Ser-Lys-Tyr-Ser-Lys-Tyr-Leu-Asp-cyclo (Glu-Lys-Arg-Ala-Lys)-Glu-Phe-Val-Gln-Trp-Leu-Met-Asn-Thr-Cys-$NH_2$; (SEQ ID NO: 2)

wherein the method for preparing a physiologically active polypeptide represented by Chemical Formula 2 or a pharmaceutically acceptable salt thereof includes:

(1) a reaction step of obtaining a peptide-resin composite by reacting the resin composite compound of Chemical Formula 3 with an amino acid; and (2) a cleavage step of cleaving the physiologically active polypeptide of Chemical Formula 2 from the peptide-resin composite.

Advantageous Effects

The novel polypeptide intermediate and the method for preparing the same according to the present invention can provide a novel polypeptide intermediate that can be used for physiologically active polypeptide pharmaceuticals, and are suitable for mass production and have the advantage of being able to produce efficient and high-quality products with reproducibility.

DESCRIPTION OF DRAWINGS

FIG. 1 refers to a chromatogram comparing the distribution of each target compound produced after cleavage of the protecting group and the resin in the Example and Comparative Example.

DETAILED DESCRIPTION OF PREFERRED EMBODIMENTS

The method for preparing the novel polypeptide intermediate of the present invention will be described in more detail step by step as follows.

The protecting group of the amino acid used herein may be any one which has stability under the conditions of the peptide condensation reaction, can be easily removed, does not affect the peptide chain and the substituents during the removal reaction, and does not cause racemization of any chiral center present in the peptide. Examples of the suitable protecting groups include 9-fluorenylmethyloxycarbonyl (Fmoc), 2-(4-nitrophenyl-sulfonyl) ethoxycarbonyl (NSC), t-butoxycarbonyl (Boc), benzyloxycarbonyl (Cbz), biphenylisopropyl-oxycarbonyl, t-amyloxycarbonyl, isobornyloxycarbonyl, ($\alpha$,$\alpha$)-dimethyl-3,5-dimethoxybenzyloxycarbonyl, O-nitrophenylsulfenyl, 2-cyano-t-butyloxycarbonyl, etc., but are not limited thereto, and other suitable protecting groups known in the art for this purpose may also be used within the scope of the present invention. Preferably, 9-fluorenylmethyloxycarbonyl (Fmoc) or t-butoxycarbonyl (Boc) may be used.

In addition, in one embodiment of the present invention, a solid-phase peptide synthesis method using 9-fluorenylmethoxycarbonyl (Fmoc) as an amino acid protecting group may be used among the amino acid protecting groups.

The resin used in all steps of the reaction of the present invention is a polymer support treated with an appropriate linker, and a polystyrene (PS)-based resin or a polystyrene-polyethylene glycol copolymer (PS-PEG copolymer)-based resin is preferable, but the resin is not limited thereto, and other suitable resins known in the art for this purpose may also be used within the scope of the present invention.

The resin that can be used in the present invention may include polystyrene (PS)-based resins such as aminomethyl resin, aminoethyl resin, aminobutyl resin, Rink amide aminomethyl resin, Rink amide aminoethyl resin, Rink amide aminobutyl resin, Rink amide MBHA resin, Rink amide resin, 2-chlorotrityl-N-Fmoc-hydroxylamine resin, HMPA-AM resin, HMPB resin, 2-chlorotrityl resin, 4-carboxytrityl resin, Wang resin, PAL resin, 4-(hydroxymethyl) phenoxyacetic acid resin, and Sieber amide resin, and polystyrene-polyethylene glycol copolymer-based resins such as such as TentaGel S resin, TentaGel R resin, TentaGel XV resin, TentaGel MB resin, TentaGel HL resin, TentaGel B resin, TentaGel M resin, TentaGel N resin, TentaGel PAP resin, Rink amide TentaGel S resin (TentaGel S RAM), Rink amide TentaGel R resin (TentaGel R RAM), Rink amide TentaGel XV resin (TentaGel XV-RAM), Rink amide TentaGel MB resin (TentaGel MB-RAM), Rink amide TentaGel HL resin (TentaGel HL RAM), Rink amide TentaGel B resin (TentaGel B RAM), Rink amide TentaGel M resin (TentaGel M RAM), Rink amide TentaGel N resin (TentaGel N RAM), Rink amide TentaGel PAP resin (TentaGel PAP RAM), and various substituted HypoGel 200 and 400 resins.

The polar aprotic solvent used in all steps of the reaction of the present invention may include, but is not limited to, for example, dimethylformamide, dimethylacetamide, etc., and other suitable polar aprotic solvents known in the art for this purpose may also be used within the scope of the present invention.

According to one embodiment of the present invention, the polar aprotic solvent used in all steps of the reaction of the present invention may be preferably selected from the group consisting of dimethylformamide, dimethylacetamide, and mixtures thereof.

Another aspect of the present invention provides a method for preparing a resin composite compound of Chemical Formula 3. The method for preparing the resin composite compound of the present invention includes the steps of:

(1) swelling a resin in a polar aprotic solvent;

(2) coupling by adding an activated and protected amino acid to the deprotected resin in a reactor;

(3) repeating step (2) until a peptide is formed;

(4) preparing a partially deprotected resin by reacting the synthesized peptide with tetrakispalladium, N-methylaniline, and phenylsilane in a solvent; and (5) cyclizing the synthesized peptide by adding a coupling reagent in a polar aprotic solvent.

In the embodiment of the present invention, the method for preparing the peptide intermediate compound of Chemical Formula 1 and the resin of Chemical Formula 3 will be described in more detail step by step as follows.

In step (1), the resin is swollen in a polar aprotic solvent.

In order to obtain the deprotected resin of step (2), the deprotected resin may be prepared by removing the protecting group using, for example, a piperidine solution in a polar aprotic solvent.

More specifically, after the deprotection reaction for preparing the deprotected resin, the deprotected resin may be washed using a polar solvent. The polar solvent used herein may be selected from the group consisting of dimethylformamide, dimethylacetamide, methanol, ethanol, and mixtures thereof. Accordingly, the deprotected resin can be activated. In a more specific embodiment, the protected amino acid is activated by adding the protected amino acid, 1-hydroxy-1H-benzotriazole, and 1,3-diisopropylcarbodiimide in a polar aprotic solvent.

In step (2), a coupling reaction is performed by adding an activated protected amino acid solution to the deprotected resin in a reactor.

In a more specific embodiment, after the coupling reaction of step (4), the coupled resin may be washed using a polar solvent. The polar solvent used herein may be selected from the group consisting of dimethylformamide, dimethylacetamide, methanol, ethanol, and mixtures thereof.

In step (3), the above steps (1)-(2) are repeatedly performed until a peptide is formed.

The reaction of step (3) may be repeated 2 to 100 times until a peptide of a desired length is formed, preferably 10 to 50 times, and most preferably 14 to 30 times.

In step (4), a partially deprotected resin is prepared by reacting the synthesized peptide with tetrakispalladium, N-methylaniline, and phenylsilane in a solvent.

The solvent used in the reaction of step (4) may be selected from the group consisting of dichloromethane, chloroform, and mixtures thereof.

In step (5), a polypeptide intermediate is prepared by performing a cyclization reaction by adding the synthesized peptide and a coupling reagent in a polar aprotic solvent.

The coupling reagent used in the reaction of step (5) may be selected from 1-hydroxy-1H-benzotriazole/1,3-diisopropylcarbodiimide or HATU (1-[bis(dimethylamino)methylene]-1H-1,2,3-triazolo[4,5-b]-pyridinium 3-oxide hexafluorophosphate)/N, N-diisopropylethylamine, but is not limited thereto, and other suitable coupling reagents known in the art for this purpose may also be used within the scope of the present invention.

Still another aspect of the present invention provides a method for preparing a physiologically active polypeptide represented by Chemical Formula 2 below or a pharmaceutically acceptable salt thereof from the method described above. The method for preparing a physiologically active polypeptide of Chemical Formula 2 and a pharmaceutically acceptable salt according to the present invention may include:

(1) a reaction step of obtaining a peptide-resin composite by reacting the resin composite compound of Chemical Formula 3 with an amino acid; and (2) a cleavage step of cleaving the physiologically active polypeptide of Chemical Formula 2 from the peptide-resin composite:

[Chemical Formula 2]
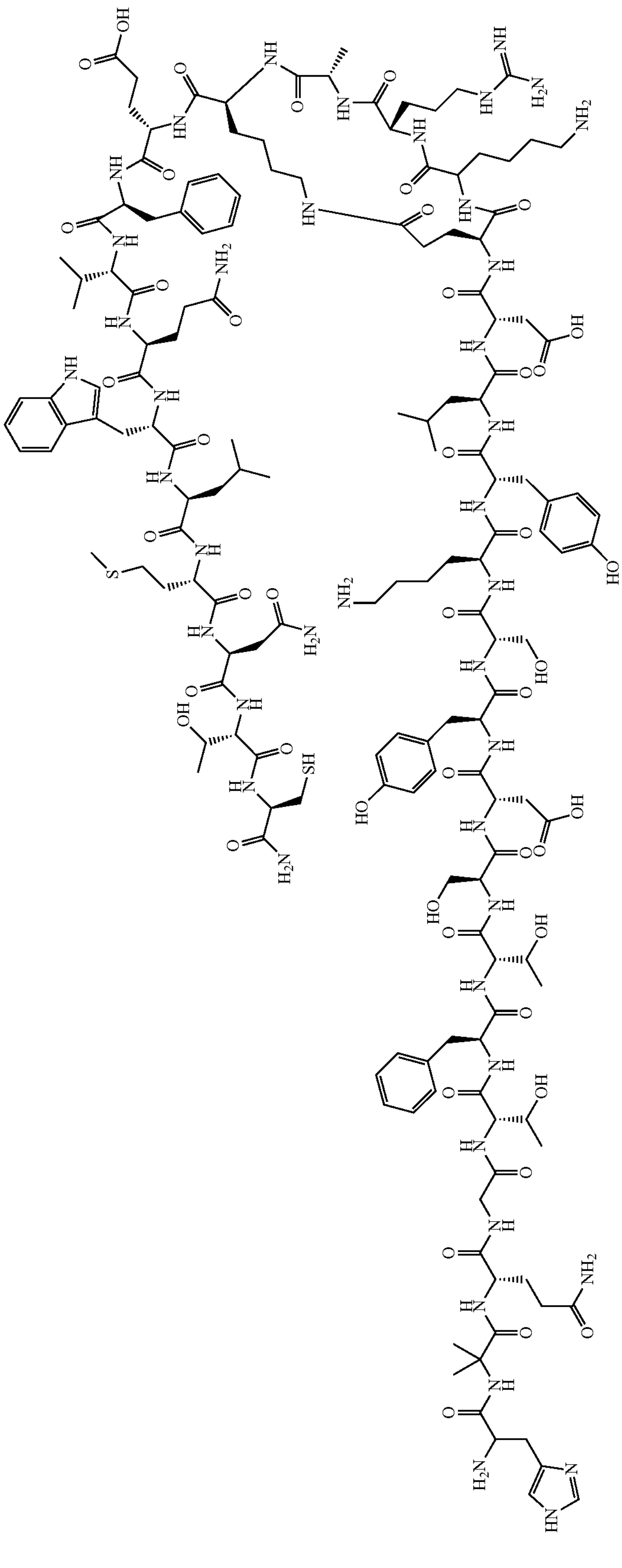

H-His-Aib-Gln-Gly-Thr-Phe-Thr-Ser-Asp-Tyr-Ser-Lys-Tyr-Ser-Lys-Tyr-Leu-Asp-cyclo (Glu-Lys-Arg-Ala-Lys)-Glu-Phe-Val-Gln-Trp-Leu-Met-Asn-Thr-Cys-$NH_2$. (SEQ ID NO: 2)

The method for preparing a physiologically polypeptide using the novel polypeptide intermediate of the present invention will be described in more detail step by step as follows. In step (1), an amino acid linking reaction is repeatedly performed until a peptide having a desired amino acid sequence is formed by reacting the resin composite compound of Chemical Formula 3 obtained by way of the above method or another method with an amino acid. The reaction of step (1) may be repeatedly performed 1 to 50 times until a peptide of a desired length is formed, and preferably 1 to 30 times.

In one embodiment of the present invention, the physiologically polypeptide of Chemical Formula 2 is in the form of a trifluoroacetic acid salt or an acetic acid salt.

In one embodiment of the method for preparing a physiologically active polypeptide of the present invention, the reaction step (1) described above may include a step of deprotecting the peptide-resin composite in a polar aprotic solvent. In a more specific embodiment, the polar aprotic solvent may be selected from the group consisting of dimethylformamide, dimethylacetamide, and mixtures thereof.

In one embodiment of the method for preparing a physiologically active polypeptide of the present invention, as the resin composite compound of Chemical Formula 3 used in the reaction step (1) described above, those in which X' is a Rink amide resin may be used.

In step (2), the desired peptide is cleaved from the resin while deprotecting the protected resin using a cleavage cocktail simultaneously.

The cleavage cocktail of step (2) may include a solution of trifluoroacetic acid (TFA), at least one scavenger, and dichloromethane.

The scavenger of step (2) may be selected from the group consisting of triisopropylsilane (TIPS), triethylsilane (TES), phenol, anisole, thioanisole, water, ethanedithiol (EDT), 1-dodecanethiol, dithiothreitol (DTT), and indole, but is not limited thereto, and other suitable scavengers known in the art for this purpose may also be used within the scope of the present invention.

The preparation method of the present invention may further include a step of filtering the cleaved mixture from the resin after step (2).

The preparation method of the present invention provides the compound of Chemical Formula 1 and the resin composite compound of Chemical Formula 3, which are novel cyclized polypeptide intermediates that can be used as high-purity pharmaceutical intermediates. When the cyclized intermediate of the present invention is used, the improvement in yield and inhibition in impurity generation may be simultaneously achieved in the preparation of physiologically active polypeptides. In addition, as compared with the prior art, the generated related substances are changed to a type that can be easily separated from the product, so that the final purification can be easily performed to thereby obtain high-quality pharmaceuticals.

In the preparation of a polypeptide having a lactam ring, the process of the cyclization reaction after linear synthesis, which is a conventional method, will be compared in more detail with the preparation method of the present invention. In the prior art method, 16 to 30 amino acids were linearly synthesized in sequence, and each linearly synthesized polypeptide (16mer to 30mer) was subject to a cyclization reaction. However, in the prior art, as the length of the linearly synthesized polypeptide increased, the purity tended to decrease sharply. In addition, as the cyclization reaction was performed at the end, impurities were generated in excess, which further decreased the purity, and the removal of heavy metals used in the cyclization synthesis must be managed, making the final purification process very difficult. Accordingly, there was a large loss in yield.

The novel polypeptide intermediate according to the present invention and the physiologically active polypeptide prepared by way of the preparation method thereof are subjected to a cyclization reaction after preparing a linear polypeptide up to 15mer, and the remaining amino acids are further synthesized. Thus, it has the advantage of synthesizing high-purity products compared with the existing preparation method. Additionally, the preparation method of the present invention also improves the generation of related substances, and thus, the final purification process after completion of synthesis can be carried out easily, and the components of heavy metals can be easily managed. This is a beneficial effect beyond what is expected when simply changing the position of the lactam cyclization process, assuming that other factors remain unchanged. The preparation method of the present invention has the advantage being an efficient process suitable for commercial production because the overall yield and purity are greatly improved.

MODE FOR CARRYING OUT THE INVENTION

Hereinafter, preferred Examples are provided to aid understanding of the present invention. However, these Examples are provided for illustrative purposes only, and it is apparent to those skilled in the art that various modifications and variations are possible within the scope and spirit of the present invention.

Throughout the present specification, one-letter or three-letter codes are typically used for naturally occurring amino acids, and generally accepted three-letter codes are used for other amino acids, such as Aib (α-aminoisobutyric acid). In addition, amino acids referred to by abbreviation herein have been described according to the IUPAC-IUB nomenclature.

alanine—Ala, A; arginine—Arg, R; asparagine—Asn, N; aspartic acid—Asp, D; cysteine—Cys, C; glutamic acid—Glu, E;
glutamine—Gln, Q; glycine—Gly, G; histidine—His, H; isoleucine—Ile, I; leucine—Leu, L; lysine—Lys, K;
methionine—Met, M; phenylalanine—Phe, F; proline—Pro, P;
serine—Ser, S; threonine—Thr, T; tryptophan—Trp, W; tyrosine—Tyr, Y; valine—Val, V Solid-phase peptide synthesis methods (SPPS methods, including methods for deprotecting amino acids, methods for cleaving peptides from resins, and purification thereof), as well as methods for detection and characterization of the resulting peptides (LCMS, MALDI, and UPLC) method) are related.

The protected amino acid derivative used is the standard Fmoc-amino acid. The alpha amino group at the N-terminal amino acid has been protected with Boc (e.g., Boc-His (Boc)-OH, or Boc-His(Trt)-OH for peptides having His at the N-terminus).

[Synthesis of Resin-Bound Peptides]

Example 1: Preparation of Rink Amide MBHA Resin 80.0 g (0.31 mmol/g) of Rink amide MBHA resin and 480 mL of dimethylformamide were added to a vessel, stirred for 15 minutes, and then filtered to remove dimethylformamide. This process was performed twice. Through the above process, a Rink amide MBHA resin was prepared.

Example 2: Preparation of Polypeptides (Synthesis of 1mer to 15mer)

Synthesis 1) Preparation of Resin-Cys(Trt)-Fmoc (Synthesis of Poly 1mer)

Step (1): Preparation of Fmoc Deprotection 480 mL of 20% piperidine was added to the resin prepared in Example 1, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected Rink amide MBHA resin, was obtained.

Step (2) Activation of Cys(Trt)-Fmoc (C)

In a vessel, 43.6 g of Cys(Trt)-Fmoc, 16.7 g of 1H-benzotriazole, 1-hydroxy, hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Cys(Trt)-Fmoc, was activated.

Step (3): Preparation of Resin-Cys(Trt)-Fmoc (Synthesis of Poly 1mer)

Cys(Trt)-Fmoc activated in step (2) was added to the Fmoc-deprotected Rink amide MBHA resin prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Fmoc, was obtained.

Synthesis 2) Preparation of Resin-Cys(Trt)-Thr(tBu)-Fmoc (Synthesis of Poly 2mer)

Step (1): Preparation of Fmoc Deprotection 480 mL of 20% piperidine was added to the polypeptide (poly 2mer synthesis) prepared in Synthesis 1 above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt) was obtained.

Step (2): Activation of Thr(tBu)-Fmoc(T)

In a vessel, 29.6 g of Thr(tBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Thr(tBu)-Fmoc, was activated.

Step (3): Preparation of Resin-Cys(Trt)-Thr(tBu)-Fmoc (Synthesis of Poly 2mer)

Thr(tBu)-Fmoc activated in step (2) was added to the Fmoc-deprotected resin-Cys(Trt) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Fmoc (C), was obtained.

Synthesis 3) Preparation of Resin-Cys(Trt)-Thr(tBu)-Asn (Trt)-Fmoc (Synthesis of Poly 3mer)

Step (1): Preparation of Fmoc Deprotection 480 mL of 20% piperidine was added to the polypeptide (synthesis of poly 2mer) prepared in Synthesis 2 above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu) was obtained.

Step (2): Activation of Asn(Trt)-Fmoc(N)

In a vessel, 44.4 g of Asn(Trt)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Thr(tBu)-Fmoc, was activated.

Step (3): Preparation of Resin-Cys(Trt)-Thr(tBu)-Asn(Trt)-Fmoc (Synthesis of Poly 3mer)

Asn(Trt)-Fmoc activated in step (2) was added to the Fmoc-deprotected resin-Cys(Trt)-Thr(tBu) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn (Trt)-Fmoc, was obtained.

Synthesis 4) Synthesis of Resin-Cys(Trt)-Thr(tBu)-Asn (Trt)-Met-Fmoc (SEQ ID NO: 3) (Synthesis of Poly 4mer)

Step (1): Preparation of Fmoc Deprotection 480 mL of 20% piperidine was added to the polypeptide (synthesis of poly 3mer) prepared in Synthesis 3) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt) was obtained.

Step (2): Activation of Met-Fmoc (M)

In a vessel, 27.6 g of Met-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Met-Fmoc, was activated.

Step (3): Preparation of Resin-Cys(Trt)-Thr(tBu)-Asn(Trt)-Met-Fmoc (SEQ ID NO: 3) (Synthesis of Poly 4mer)

Met-Fmoc activated in step (2) was added to the Fmoc-deprotected resin-Cys(Trt)-Thr(tBu)-Asn(Trt) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn (Trt)-Met-Fmoc (SEQ ID NO: 3), was obtained.

Synthesis 5) Preparation of Resin-Cys(Trt)-Thr(tBu)-Asn (Trt)-Met-Leu-Fmoc (SEQ ID NO: 4) (Synthesis of Poly 5mer)

Step (1): Preparation of Fmoc Deprotection 480 mL of 20% piperidine was added to the polypeptide (synthesis of poly 4mer) prepared in Synthesis 4) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn (Trt)-Met (SEQ ID NO: 3) was obtained.

Step (2): Activation of Leu-Fmoc(L)

In a vessel, 26.3 g of Leu-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Leu-Fmoc, was activated.

Step (3): Preparation of Resin-Cys(Trt)-Thr(tBu)-Asn(Trt)-Met-Leu-Fmoc (SEQ ID No: 4) (Synthesis of Poly 5mer)

Leu-Fmoc activated in step (2) was added to the Fmoc-deprotected resin-Cys(Trt)-Thr(tBu)-Asn(Trt)-Met (SEQ ID NO: 3) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys (Trt)-Thr(tBu)-Asn(Trt)-Met-Leu-Fmoc (SEQ ID NO: 4), was obtained.

Synthesis 6) Preparation of Resin-Cys(Trt)-Thr(tBu)-Asn (Trt)-Met-Leu-Trp(Boc)-Fmoc (SEQ ID NO: 5) (Synthesis of Poly 6mer)

Step (1): Preparation of Fmoc Deprotection 480 mL of 20% piperidine was added to the polypeptide (synthesis of poly 5mer) prepared in Synthesis 5) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn (Trt)-Met-Leu (SEQ ID NO: 4) was obtained.

Step (2): Activation of Trp(Boc)-Fmoc(W)

In a vessel, 39.2 g of Trp(Boc)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Trp(Boc)-Fmoc, was activated.

Step (3): Preparation of Resin-Cys(Trt)-Thr(tBu)-Asn(Trt)-Met-Leu-Trp(Boc)-Fmoc (SEQ ID NO: 5) (Synthesis of Poly 6mer)

Trp(Boc)-Fmoc activated in step (2) was added to the Fmoc-deprotected resin-Cys(Trt)-Thr(tBu)-Asn(Trt)-Met-Leu (SEQ ID NO: 4) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp (Boc)-Fmoc (SEQ ID NO: 5), was obtained.

Synthesis 7) Preparation of Resin-Cys(Trt)-Thr(tBu)-Asn (Trt)-Met-Leu-Trp(Boc)-Gln(Trt)-Fmoc (SEQ ID NO: 6) (Synthesis of Poly 7mer)

Step (1): Preparation of Fmoc Deprotection 480 mL of 20% piperidine was added to the polypeptide (synthesis of poly 6mer) prepared in Synthesis 6) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn (Trt)-Met-Leu-Trp(Boc) (SEQ ID NO: 5) was obtained.

Step (2): Activation of Gln(Trt)-Fmoc(Q)

In a vessel, 45.4 g of Gln(Trt)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Gln(Trt)-Fmoc, was activated.

Step (3): Preparation of Resin-Cys(Trt)-Thr(tBu)-Asn(Trt)-Met-Leu-Trp(Boc)-Gln(Trt)-Fmoc (SEQ ID NO: 6) (Synthesis of Poly 7mer)

Gln(Trt)-Fmoc activated in step (2) was added to the Fmoc-deprotected resin-Cys(Trt)-Thr(tBu)-Asn(Trt)-Met-Leu-Trp(Boc) (SEQ ID NO: 5) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Fmoc (SEQ ID NO: 6), was obtained.

Synthesis 8) Preparation of Resin-Cys(Trt)-Thr(tBu)-Asn(Trt)-Met-Leu-Trp(Boc)-Gln(Trt)-Val-Fmoc (SEQ ID NO: 7) (Synthesis of Poly 8mer)

Step (1): Preparation of Fmoc Deprotection 480 mL of 20% piperidine was added to the polypeptide (synthesis of poly 7mer) prepared in Synthesis 7) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt) (SEQ ID NO: 6) was obtained.

Step (2): Activation of Val-Fmoc(V)

In a vessel, 45.4 g of Val-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Val-Fmoc, was activated.

Step (3): Preparation of Resin-Cys(Trt)-Thr(tBu)-Asn(Trt)-Met-Leu-Trp(Boc)-Gln(Trt)-Val-Fmoc (SEQ ID NO:7) (Synthesis of Poly 8mer)

Val-Fmoc activated in step (2) was added to the Fmoc-deprotected resin-Cys(Trt)-Thr(tBu)-Asn(Trt)-Met-Leu-Trp(Boc)-Gln(Trt) (SEQ ID NO: 6) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Fmoc (SEQ ID NO: 7), was obtained.

Synthesis 9) Preparation of Resin-Cys(Trt)-Thr(tBu)-Asn(Trt)-Met-Leu-Trp(Boc)-Gln(Trt)-Val-Phe-Fmoc (SEQ ID NO: 8) (Synthesis of Poly 9mer)

Step (1): Preparation of Fmoc Deprotection 480 mL of 20% piperidine was added to the polypeptide (synthesis of poly 8mer) prepared in Synthesis 8) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val (SEQ ID NO: 7) was obtained.

Step (2): Activation of Phe-Fmoc(F)

In a vessel, 28.2 g of Phe-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Phe-Fmoc, was activated.

Step (3): Preparation of Resin-Cys(Trt)-Thr(tBu)-Asn(Trt)-Met-Leu-Trp(Boc)-Gln(Trt)-Val-Phe-Fmoc (SEQ ID NO: 8) (Synthesis of Poly 9mer)

Phe-Fmoc activated in step (2) was added to the Fmoc-deprotected resin-Cys(Trt)-Thr(tBu)-Asn(Trt)-Met-Leu-Trp(Boc)-Gln(Trt)-Val (SEQ ID NO: 7) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Fmoc (SEQ ID NO: 8), was obtained.

Synthesis 10) Preparation of Resin-Cys(Trt)-Thr(tBu)-Asn(Trt)-Met-Leu-Trp(Boc)-Gln(Trt)-Val-Phe-Glu(OtBu)-Fmoc (SEQ ID NO: 9) (Synthesis of Poly 10mer)

Step (1): Preparation Fmoc Deprotection 480 mL of 20% piperidine was added to the polypeptide (synthesis of poly 9mer) prepared in Synthesis 9) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val (SEQ ID NO: 7) was obtained.

Step (2): Activation of Glu(OtBu)-Fmoc (E)

In a vessel, 31.6 g of Glu(OtBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Glu(OtBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-Fmoc (SEQ ID NO: 9) (Synthesis of Poly 10mer)

Glu(OtBu)-Fmoc activated in step (2) was added to the Fmoc-deprotected resin-Cys(Trt)-Thr(tBu)-Asn(Trt)-Met-Leu-Trp(Boc)-Gln(Trt)-Val-Phe (SEQ ID NO: 8) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 ml of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-Fmoc (SEQ ID NO: 9), was obtained.

Synthesis 11) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Fmoc (SEQ ID NO: 10) (Synthesis of Poly 11mer)

Step (1): Preparation of Fmoc Deprotection 480 mL of 20% piperidine was added to the polypeptide (synthesis of poly 10mer) prepared in Synthesis 10) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu) (SEQ ID NO: 9) was obtained.

Step (2): Activation of Lys(Alloc)-Fmoc(K)

In a vessel, 33.7 g of Lys(Alloc)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Lys(Alloc)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Fmoc (SEQ ID NO: 10) (Synthesis of Poly 11mer)

Lys(Alloc)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu) (SEQ ID NO: 9) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-Lys(Alloc)-Fmoc (SEQ ID NO: 10), was obtained.

Synthesis 12) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Fmoc (SEQ ID NO: 11) (Synthesis of Poly 12mer)

Step (1): Preparation of Fmoc Deprotection 480 mL of 20% piperidine was added to the polypeptide (synthesis of poly 11mer) prepared in Synthesis 11) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc) (SEQ ID NO: 10) was obtained.

Step (2): Activation of Ala-Fmoc(A)

In a vessel, 23.2 g of Ala-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Ala-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Fmoc (SEQ ID NO: 11) (Synthesis of Poly 12mer)

Ala-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc) (SEQ ID NO: 10) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gin (Trt)-Val-Phe-Glu(OtBu)-Lys(Alloc)-Ala-Fmoc (SEQ ID NO: 11), was obtained.

Synthesis 13) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Fmoc (SEQ ID NO: 12) (Synthesis of Poly 13mer)

Step (1): Preparation of Fmoc Deprotection 480 mL of 20% piperidine was added to the polypeptide (synthesis of poly 12mer) prepared in Synthesis 12) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala (SEQ ID NO: 11), was obtained.

Step (2): Activation of Arg(Pbf)-Fmoc(R)

In a vessel, 48.3 g of Arg(Pbf)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Arg(Pbf)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Fmoc (SEQ ID NO: 12) (Synthesis of Poly 13mer)

Arg(Pbf)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala (SEQ ID NO: 11) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Fmoc (SEQ ID NO: 12), was obtained.

Synthesis 14) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Fmoc (SEQ ID NO: 13) (Synthesis of Poly 14mer)

Step (1): Preparation of Fmoc Deprotection 480 mL of 20% piperidine was added to the polypeptide (synthesis of poly 13mer) prepared in Synthesis 13) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf) (SEQ ID NO: 12), was obtained.

Step (2): Activation of Lys(Boc)-Fmoc(K)

In a vessel, 34.9 g of Lys(Boc)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Lys(Boc)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Fmoc (SEQ ID NO: 13) (Synthesis of Poly 14mer)

Lys(Boc)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf) (SEQ ID NO: 12) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gin (Trt)-Val-Phe-Glu(OtBu)-Lys(Alloc)-Ala-Arg(Pbf)-Lys(Boc)-Fmoc (SEQ ID NO: 13), was obtained.

Synthesis 15) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Fmoc (SEQ ID NO: 14) (Synthesis of Poly 15mer)

Step (1): Preparation of Fmoc Deprotection 480 mL of 20% piperidine was added to the polypeptide (synthesis of poly 14mer) prepared in Synthesis 14) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc) (SEQ ID NO: 13) was obtained.

Step (2): Activation of Glu(OAll)-Fmoc(E)

In a vessel, 30.5 g of Glu(OAll)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Glu(OAll)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Fmoc (SEQ ID NO: 14) (Synthesis of Poly 15mer)

Glu(OAll)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc) (SEQ ID NO: 13) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Fmoc (SEQ ID NO: 14), was obtained.

Example 3: Preparation of Cyclized Polypeptide

Step (1): Preparation of Partially Deprotection (Alloc/OAll)

In a vessel, 11.5 g of tetrakispalladium and 800 mL of dichloromethane were added, and the mixture was completely dissolved by stirring. 78.6 mL of N-methylaniline and 38.5 mL of phenylsilane were added to the dissolved reaction solution, and the mixture was stirred for 5 minutes. 480 mL of dichloromethane was added to the polypeptide (synthesis of poly 15mer) prepared in Synthesis 15), stirred for 2 minutes, and then filtered. This process was performed three times. The thus-prepared reaction solution was added to the filtered resin, stirred at room temperature for 5 hours, and then filtered. 480 mL of dichloromethane was added to the filtered resin, stirred for 2 minutes, and then filtered. This process was performed five times. 480 mL of methanol was added to the filtered resin, stirred for 2 minutes, and then filtered. This process was performed twice.

The cyclization step can be carried out by way of the process of either (2)-1 or (2)-2 below.

Step (2)-1: Preparation of Cyclized Polypeptide (Synthesis of Cyclized Poly 15mer)

In a vessel, 1H-benzotriazole, 1-hydroxy, 26.8 g of hydrate and 480 mL of dimethylformamide were added, and the mixture was completely dissolved by stirring. 27.2 mL of 1,3-diisopropylcarbodiimide was added to the dissolved reaction solution and stirred at room temperature for 5 minutes. The thus-prepared reaction solution was added to the polypeptide (partially deprotected 15mer) prepared in step (1), stirred at room temperature for 5 hours, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Fmoc (SEQ ID NO: 33), was obtained.

Step (2)-2: Preparation of Cyclized Polypeptide (Synthesis of Cyclized Poly 15mer)

In a reaction vessel, 480 mL of dimethylformamide and 56.6 g of HATU (1-[bis(dimethylamino)methylene]-1H-1,2,3-triazolo[4,5-b]-pyridinium 3-oxide) hexafluorophosphate) were added, and the mixture was completely dissolved by stirring. 51.8 mL of N, N-diisopropylethylamine was added to the dissolved reaction solution and stirred at room temperature for 5 minutes. The thus-prepared reaction solution was added to the polypeptide (partially deprotected 15mer) prepared in step (1), stirred at room temperature for 3 hours, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Fmoc (SEQ ID NO: 33), was obtained.

Example 4: Preparation of Cyclized Polypeptides (Synthesis of 16 to 30mer)

Synthesis 1) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Fmoc (SEQ ID NO: 34) (Synthesis of Cyclized Poly 16mer)

Step (1): Preparation of Fmoc Deprotection 480 mL of 20% piperidine was added to the cyclized polypeptide (synthesis of cyclized poly 15mer) prepared in Example 3 above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu] (SEQ ID NO: 33), was obtained.

Step (2): Activation of Asp(OtBu)-Fmoc (D)

In a vessel, 30.6 g of Asp(OtBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Asp(OtBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Fmoc (SEQ ID NO: 34) (Synthesis of Cyclized Poly 16mer)

Asp(OtBu)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu] (SEQ ID NO: 33) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Fmoc (SEQ ID NO: 34), was obtained.

Synthesis 2) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Fmoc (SEQ ID NO: 35) (Synthesis of Cyclized Poly 17mer)

Step (1): Preparation of Fmoc Deprotection 480 mL of 20% piperidine was added to the cyclized polypeptide (synthesis of cyclized poly 16mer) prepared in Synthesis 1) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu) (SEQ ID NO: 34), was obtained.

Step (2): Activation of Leu-Fmoc(L)

In a vessel, 26.3 g of Leu-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Leu-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Fmoc (SEQ ID NO: 35) (Synthesis of Cyclized Poly 17mer)

Leu-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu) (SEQ ID NO: 34) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Fmoc (SEQ ID NO: 35), was obtained.

Synthesis 3) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Fmoc (SEQ ID NO: 36) (Synthesis of Cyclized Poly 18mer)

Step (1): Preparation of Fmoc Deprotection 480 mL of 20% piperidine was added to the cyclized polypeptide (synthesis of cyclized poly 17mer) prepared in Synthesis 2) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu (SEQ ID NO: 35), was obtained.

Step (2): Activation of Tyr(tBu)-Fmoc(Y)

In a vessel, 34.2 g of Tyr(tBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Tyr(tBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Fmoc (SEQ ID NO: 36) (Synthesis of Cyclized Poly 18mer)

Tyr(tBu)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu (SEQ ID NO: 35) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Fmoc (SEQ ID NO: 36), was obtained.

Synthesis 4) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Fmoc (SEQ ID NO: 37) (Synthesis of Cyclized Poly 19mer)

Step (1): Preparation of Fmoc Deprotection 480 mL of 20% piperidine was added to the cyclized polypeptide (synthesis of cyclized poly 18mer) prepared in Synthesis 3) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu) (SEQ ID NO: 36), was obtained.

Step (2): Activation of Lys(Boc)-Fmoc(K)

In a vessel, 34.9 g of Lys(Boc)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Lys(Boc)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Fmoc (SEQ ID NO: 37) (Synthesis of Cyclized Poly 19mer)

Lys(Boc)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu) (SEQ ID NO: 36) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Fmoc (SEQ ID NO: 37), was obtained.

Synthesis 5) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Fmoc (SEQ ID NO: 38) (Synthesis of Cyclized Poly 20mer)

Step (1): Preparation of Fmoc Deprotection 480 mL of 20% piperidine was added to the cyclized polypeptide (synthesis of cyclized poly 19mer) prepared in Synthesis 4) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc) (SEQ ID NO: 37), was obtained.

Step (2): Activation of Ser(tBu)-Fmoc(S)

In a vessel, 28.5 g of Ser(tBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Ser(tBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Fmoc (SEQ ID NO: 38) (Synthesis of Cyclized Poly 20mer)

Ser(tBu)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc) (SEQ ID NO: 37) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp (Boc)-Gln(Trt)-Val-Phe-Glu(OtBu)-cyclo[Lys-Ala-Arg (Pbf)-Lys(Boc)-Glu]-Asp(OtBu)-Leu-Tyr(tBu)-Lys(Boc)-Ser(tBu)-Fmoc (SEQ ID NO: 38), was obtained.

Synthesis 6) Preparation of Resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Fmoc (SEQ ID NO: 39) (Synthesis of Cyclized Poly 21mer)

Step (1): Preparation of Fmoc Deprotection 480 mL of 20% piperidine was added to the cyclized polypeptide (synthesis of cyclized poly 20mer) prepared in Synthesis 5) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu) (SEQ ID NO: 38), was obtained.

Step (2): Activation of Tyr(tBu)-Fmoc (Y)

In a vessel, 34.2 g of Tyr(tBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Tyr(tBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Tyr(tBu)-Fmoc (SEQ ID NO: 39) (Synthesis of Cyclized Poly 21mer)

Tyr(tBu)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu) (SEQ ID NO: 38) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Fmoc (SEQ ID NO: 39), was obtained.

Synthesis 7) Preparation of Resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Asp(OtBu)-Fmoc (SEQ ID NO: 40) (Synthesis of Cyclized Poly 22mer)

Step (1): Preparation of Fmoc Deprotection 480 mL of 20% piperidine was added to the cyclized polypeptide (synthesis of cyclized poly 21mer) prepared in Synthesis 6) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu) (SEQ ID No: 39), was obtained.

Step (2): Activation of Asp(OtBu)-Fmoc(D)

In a vessel, 30.6 g of Asp(OtBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Asp(OtBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Tyr(tBu)-Asp(OtBu)-Fmoc (SEQ ID NO: 40) (Synthesis of Cyclized Poly 22mer)

Asp(OtBu)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Tyr(tBu) (SEQ ID NO: 39) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Fmoc (SEQ ID NO: 40), was obtained.

Synthesis 8) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Fmoc (SEQ ID NO: 41) (Synthesis of Cyclized Poly 23mer)

Step (1): Preparation of Fmoc Deprotection 480 mL of 20% piperidine was added to the cyclized polypeptide (synthesis of cyclized poly 22mer) prepared in Synthesis 7) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu) (SEQ ID NO: 40), was obtained.

Step (2): Activation of Ser(tBu)-Fmoc(S)

In a vessel, 28.5 g of Ser(tBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Ser(tBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Fmoc (SEQ ID NO: 41) (Synthesis of Cyclized Poly 23mer)

Ser(tBu)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu) (SEQ ID NO: 40) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Fmoc (SEQ ID NO: 41), was obtained.

Synthesis 9) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Fmoc (SEQ ID NO: 42) (Synthesis of Cyclized Poly 24mer)

Step (1): Preparation of Fmoc Deprotection 480 mL of 20% piperidine was added to the cyclized polypeptide (synthesis of cyclized poly 23mer) prepared in Synthesis 8) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu) (SEQ ID NO: 41), was obtained.

Step (2): Activation of Thr(tBu)-Fmoc(T)

In a vessel, 29.6 g of Thr(tBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Thr(tBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu) Fmoc (SEQ ID NO: 42) (Synthesis of Cyclized Poly 24mer)

Thr(tBu)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu) (SEQ ID NO: 41) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Fmoc (SEQ ID NO: 42), was obtained.

Synthesis 10) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Fmoc (SEQ ID NO: 43) (Synthesis of Cyclized Poly 25mer)

Step (1): Preparation of Fmoc Deprotection 480 mL of 20% piperidine was added to the cyclized polypeptide (synthesis of cyclized poly 24mer) prepared in Synthesis 9) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp (OtBu)-Ser(tBu)-Thr(tBu) (SEQ ID NO: 42), was obtained.

Step (2): Activation of Phe-Fmoc(F)

In a vessel, 28.8 g of Phe-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Phe-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Tyr(tBu)-Asp(OtBu)-Ser(tBu)-Thr(tBu)-Phe-Fmoc (SEQ ID NO: 43) (Synthesis of Cyclized Poly 25mer)

Phe-Fmoc activated in step (2) was added to the Fmoc-deprotected resin-Cys(Trt)-Thr(tBu)-Asn(Trt)-Met-Leu-Trp (Boc)-Gln(Trt)-Val-Phe-Glu(OtBu)-cyclo[Lys-Ala-Arg (Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu) (SEQ ID NO: 42) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp (OtBu)-Ser(tBu)-Thr(tBu)-Phe-Fmoc (SEQ ID NO: 43), was obtained.

Synthesis 11) Preparation of Resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Asp(OtBu)-Ser(tBu)-Thr(tBu)-Phe-Thr(tBu)-Fmoc (SEQ ID NO: 44) (Synthesis of Cyclized Poly 26mer)

Step (1): Preparation of Fmoc Deprotection 480 mL of 20% piperidine was added to the cyclized polypeptide (synthesis of cyclized poly 25mer) prepared in Synthesis 10) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp (OtBu)-Ser(tBu)-Thr(tBu)-Phe (SEQ ID NO: 43), was obtained.

Step (2): Activation of Thr(tBu)-Fmoc(T)

In a vessel, 29.6 g of Thr(tBu)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Thr(tBu)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Tyr(tBu)-Asp(OtBu)-Ser(tBu)-Thr(tBu)-Phe-Thr(tBu)-Fmoc (SEQ ID NO: 44) (Synthesis of Cyclized Poly 26mer)

Phe-Fmoc activated in step (2) was added to the Fmoc-deprotected resin-Cys(Trt)-Thr(tBu)-Asn(Trt)-Met-Leu-Trp (Boc)-Gln(Trt)-Val-Phe-Glu(OtBu)-cyclo[Lys-Ala-Arg (Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe (SEQ ID NO: 43) prepared in step (1), stirred at room temperature for 3 hours or more, and then filtered. 480 ml of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln (Trt)-Val-Phe-Glu(OtBu)-cyclo[Lys-Ala-Arg(Pbf)-Lys (Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr(tBu)-Fmoc (SEQ ID NO: 44), was obtained.

Synthesis 12) Preparation of Resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Asp(OtBu)-Ser(tBu)-Thr(tBu)-Phe-Thr(tBu)-Gly-Fmoc (SEQ ID NO: 45) (Synthesis of Cyclized Poly 27mer)

Step (1): Preparation of Fmoc Deprotection 480 mL of 20% piperidine was added to the cyclized polypeptide (synthesis of cyclized poly 26mer) prepared in Synthesis 11) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp (OtBu)-Ser(tBu)-Thr(tBu)-Phe-Thr(tBu) (SEQ ID NO: 44), was obtained.

Step (2): Activation of Gly-Fmoc (G)

In a vessel, 22.1 g of Gly-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Gly-Fmoc, was activated.

Step (3): Preparation of Resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Asp(OtBu)-Ser(tBu)-Thr(tBu)-Phe-Thr(tBu)-Gly-Fmoc (SEQ ID NO: 45) (Synthesis of Cyclized 27mer)

Gly-Fmoc activated in step (2) was added to the Fmoc-deprotected resin-Cys(Trt)-Thr(tBu)-Asn(Trt)-Met-Leu-Trp (Boc)-Gln(Trt)-Val-Phe-Glu(OtBu)-cyclo[Lys-Ala-Arg (Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr (tBu) (SEQ ID NO: 44) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp (Boc)-Gln(Trt)-Val-Phe-Glu(OtBu)-cyclo[Lys-Ala-Arg (Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr (tBu)-Gly-Fmoc (SEQ ID NO: 45), was obtained.

Synthesis 13) Preparation of Resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Asp(OtBu)-Ser(tBu)-Thr(tBu)-Phe-Thr(tBu)-Gly-Gln(Trt)-Fmoc (SEQ ID NO: 46) (Synthesis of Cyclized Poly 28mer)

Step (1): Preparation of Fmoc Deprotection 480 mL of 20% piperidine was added to the cyclized polypeptide (synthesis of cyclized poly 27mer) prepared in Synthesis 12) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp (OtBu)-Ser(tBu)-Thr(tBu)-Phe-Thr(tBu)-Gly (SEQ ID NO: 45), was obtained.

Step (2): Activation of Gln(Trt)-Fmoc(Q)

In a vessel, 45.4 g of Gln(Trt)-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Gln(Trt)-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Tyr(tBu)-Asp(OtBu)-Ser(tBu)-Thr(tBu)-Phe-Thr(tBu)-Gly-Gln(Trt)-Fmoc (SEQ ID NO: 46) (Synthesis of Cyclized 28mer)

Gln(Trt)-Fmoc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Tyr(tBu)-Asp(OtBu)-Ser(tBu)-Thr(tBu)-Phe-Thr(tBu)-Gly (SEQ ID NO: 45) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Asp(OtBu)-Ser(tBu)-Thr(tBu)-Phe-Thr(tBu)-Gly-Gln(Trt)-Fmoc (SEQ ID NO: 46), was obtained.

Synthesis 14) Preparation of Resin-Cys(Trt)-Thr(tBu)-Asn (Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr (tBu)-Lys(Boc)-Ser(tBu)-Tyr(tBu)-Asp(OtBu)-Ser(tBu)-Thr(tBu)-Phe-Thr(tBu)-Gly-Gln(Trt)-Aib-Fmoc (SEQ ID NO: 31) (Synthesis of Cyclized Poly 29mer)

Step (1): Preparation of Fmoc Deprotection 480 mL of 20% piperidine was added to the cyclized polypeptide (synthesis of cyclized poly 28mer) prepared in Synthesis 13) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys (Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp (OtBu)-Ser(tBu)-Thr(tBu)-Phe-Thr(tBu)-Gly-Gln(Trt) (SEQ ID NO: 46), was obtained.

Step (2): Activation of Aib-Fmoc

In a vessel, 24.2 g of Aib-Fmoc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, Aib-Fmoc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys (Boc)-Ser(tBu)-Tyr(tBu)-Asp(OtBu)-Ser(tBu)-Thr(tBu)-Phe-Thr(tBu)-Gly-Gln(Trt)-Aib-Fmoc (SEQ ID NO: 31) (Synthesis of Cyclized 29mer)

Aib-Fmoc activated in step (2) was added to the Fmoc-deprotected resin-Cys(Trt)-Thr(tBu)-Asn(Trt)-Met-Leu-Trp (Boc)-Gln(Trt)-Val-Phe-Glu(OtBu)-cyclo[Lys-Ala-Arg (Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr (tBu)-Gly-Gin (Trt) (SEQ ID NO: 46) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr(tBu)-Gly-Gln(Trt)-Aib-Fmoc (SEQ ID NO: 31), was obtained.

Synthesis 15) Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr(tBu)-Gly-Gln(Trt)-Aib-His(Trt)-Boc (SEQ ID NO: 30) (Synthesis of Cyclized Poly 30mer)

Step (1): Preparation of Fmoc Deprotection 480 mL of 20% piperidine was added to the cyclized polypeptide (synthesis of cyclized poly 29mer) prepared in Synthesis 14) above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr(tBu)-Gly-Gln(Trt)-Aib (SEQ ID NO: 31), was obtained.

Step (2): Activation of His(Trt)-Boc (H)

In a vessel, 37.0 g of His(Trt)-Boc, 16.7 g of 1-hydroxy-1H-benzotriazole hydrate, and 480 mL of dimethylformamide were added, and the mixture was completely dissolved by stirring. 15.5 mL of 1,3-diisopropylcarbodiimide was added to the dissolved reaction solution and stirred at room temperature for 30 minutes. Through the above process, the target compound, His(Trt)-Boc, was activated.

Step (3): Preparation of Resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr(tBu)-Gly-Gln(Trt)-Aib-His(Trt)-Boc (SEQ ID NO: 30) (Synthesis of Cyclized 30mer)

His(Trt)-Boc activated in step (2) was added to the Fmoc-deprotected resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr(tBu)-Gly-Gln(Trt)-Aib (SEQ ID NO: 31) prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr(tBu)-Gly-Gln(Trt)-Aib-His(Trt)-Boc (SEQ ID NO: 30), was obtained.

Example 5: Preparation of $NH_2$CO-Cys-Thr-Asn-Met-Leu-Trp-Gln-Val-Phe-Glu-cyclo[Lys-Ala-Arg-Lys-Glu]-Asp-Leu-Tyr-Lys-Ser-Tyr-Asp-Ser-Thr-Phe-Thr-Gly-Gln-Aib-His-$NH_2$ (SEQ ID NO: 32). TFA (Cleavage of Protecting Groups and Resins)

165 mL of trifluoroacetic acid, 10 mL of phenol, 10 mL of distilled water, 10 mL of thioanisole, and 5 mL of 1,2-ethanedithiol were added to Vessel 2 under nitrogen atmosphere and stirred for 10 minutes. 20 g of the dried cyclized polypeptide 30mer was added to Vessel 1, and the prepared reaction solution was added thereto, and the mixture was stirred at room temperature for 1 hour and 30 minutes. 3.0 L of methyl tertiary butyl ether was added to Vessel 3 and cooled to 0° C. to 10° C. under nitrogen atmosphere. The temperature of the reaction solution of Vessel 1 was cooled to 5° C., and 2.0 L of methyl tertiary butyl ether, which is the cooled reactant in Vessel 3, was added thereto and stirred for 10 minutes. The reaction solution was filtered and washed twice with 400 mL of the cooled methyl tertiary butyl ether. The filtered crystals were dried under nitrogen atmosphere for 10 minutes. The thus-dried crystals were added to Vessel 1, and 400 mL of distilled water was added thereto, and the mixture was stirred at room temperature for 10 minutes. The reactant was filtered and washed with 600 mL of distilled water to obtain the target compound, $NH_2$CO-Cys-Thr-Asn-Met-Leu-Trp-Gln-Val-Phe-Glu-cyclo[Lys-Ala-Arg-Lys-Glu]-Asp-Leu-Tyr-Lys-Ser-Tyr-Asp-Ser-Thr-Phe-Thr-Gly-Gln-Aib-His-$NH_2$ (SEQ ID NO: 32). TFA.

Comparative Example 1: Preparation of Rink Amide Resin 80.0 g (0.31 mmol/g) of Rink amide MBHA resin and 480 mL of dimethylformamide were added to a vessel, stirred for 15 minutes, and then filtered to remove dimethylformamide. This process was performed twice. Through the above process, Rink amide MBHA resin was prepared.

Comparative Example 2: Preparation of Polypeptides (Synthesis of 1 to 30mer)

Synthesis 1) Preparation of Resin-Cys(Trt)-Fmoc (Synthesis of Poly 1mer)

Step (1): Preparation of Fmoc Deprotection 480 mL of 20% piperidine was added to the resin prepared in Comparative Example 1 above, stirred for 20 minutes, and then filtered to remove 20% piperidine. This process was performed twice. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, Fmoc-deprotected Rink amide MBHA resin, was obtained.

Step (2): Activation of Cys(Trt)-Fmoc (C)

In a vessel, 29.1 g of Cys(Trt)-Fmoc, 1H-benzotriazole, 1-hydroxy, 13.4 g of hydrate, and 480 mL of dimethylformamide were added, and the mixture was completely dissolved by stirring. 11.6 mL of 1,3-diisopropylcarbodiimide was added to the dissolved reaction solution and stirred at room temperature for 30 minutes. Through the above process, the target compound, Cys(Trt)-Fmoc, was activated.

Step (3): Preparation of Resin-Cys(Trt)-Fmoc (Synthesis of Poly 1mer)

Cys(Trt)-Fmoc activated in step (2) was added to the Fmoc-deprotected Rink amide MBHA resin prepared in step (1), stirred at room temperature for 3 hours or more, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the above process, the target compound, resin-Cys(Trt)-Fmoc, was obtained.

Synthesis 2) Preparation of Resin-Cys(Trt)-Thr(tBu)-Fmoc (Synthesis of Poly 2mer)

Step (1): Preparation of Fmoc Deprotection

The target compound, Fmoc-deprotected resin-Cys(Trt), was obtained in the same manner as in step (1) of Synthesis 1) with the polypeptide (synthesis of poly 1mer) prepared in Synthesis 1).

Step (2): Activation of Thr(tBu)-Fmoc(T)

The target compound, Thr(tBu)-Fmoc, was activated in the same manner as in step (2) of Synthesis 1) with 19.7 g of Thr(tBu)-Fmoc.

Step (3): Preparation of Resin-Cys(Trt)-Thr(tBu)-Fmoc (Synthesis of Poly 2mer)

The target compound, resin-Cys(Trt)-Thr(tBu)-Fmoc (C), was obtained in the same manner as in step (3) of Synthesis 1).

Synthesis 3) Preparation of Resin-Cys(Trt)-Thr(tBu)-Asn (Trt)-Fmoc (Synthesis of Poly 3mer)

Step (1): Preparation of Fmoc Deprotection

The target compound, Fmoc-deprotected resin-Cys(Trt)-Thr(tBu), was obtained in the same manner as in step (1) of Synthesis 1) with the polypeptide (synthesis of poly 2mer) prepared in Synthesis 2).

Step (2): Activation of Asn(Trt)-Fmoc(N)

The target compound, Asn(Trt)-Fmoc, was activated in the same manner as in step (2) of Synthesis 1) with 29.6 g of Asn(Trt)-Fmoc.

Step (3): Preparation of Resin-Cys(Trt)-Thr(tBu)-Asn(Trt)-Fmoc (Synthesis of Poly 3mer)

The target compound, resin-Cys(Trt)-Thr(tBu)-Asn(Trt)-Fmoc, was obtained in the same manner as in step (3) of Synthesis 1).

Synthesis 4) Preparation of Resin-Cys(Trt)-Thr(tBu)-Asn (Trt)-Met-Fmoc (SEQ ID NO: 3) (Synthesis of Poly 4mer)

Step (1): Preparation of Fmoc Deprotection

The target compound, Fmoc-deprotected resin-Cys(Trt)-Thr(tBu)-Asn(Trt), was obtained in the same manner as in step (1) of Synthesis 1) with the polypeptide (synthesis of poly 3mer) prepared in Synthesis 3).

Step (2): Activation of Met-Fmoc (M)

The target compound, Met-Fmoc, was activated in the same manner as in step (2) of Synthesis 1) with 18.4 g of Met-Fmoc.

Step (3): Preparation of Resin-Cys(Trt)-Thr(tBu)-Asn(Trt)-Fmoc (Synthesis of Poly 4mer)

The target compound, resin-Cys(Trt)-Thr(tBu)-Asn(Trt)-Met-Fmoc (SEQ ID NO: 3), was obtained in the same manner as in step (3) of Synthesis 1).

Synthesis 5) Preparation of Resin-Cys(Trt)-Thr(tBu)-Asn (Trt)-Met-Leu-Fmoc (SEQ ID NO: 4) (Synthesis of Poly 5mer)

Step (1): Preparation of Fmoc Deprotection

The target compound, Fmoc-deprotected resin-Cys(Trt)-Thr(tBu)-Asn(Trt)-Met (SEQ ID NO: 3), was obtained in the same manner as in step (1) of Synthesis 1) with the polypeptide (synthesis of poly 4mer) prepared in Synthesis 4).

Step (2): Activation of Leu-Fmoc(L)

The target compound, Leu-Fmoc, was activated in the same manner as in step (2) of Synthesis 1) with 17.5 g of Leu-Fmoc.

Step (3): Preparation of Resin-Cys(Trt)-Thr(tBu)-Asn(Trt)-Met-Leu-Fmoc (SEQ ID No: 4) (Synthesis of Poly 5mer)

The target compound, resin-Cys(Trt)-Thr(tBu)-Asn(Trt)-Met-Leu-Fmoc (SEQ ID NO: 4), was obtained in the same manner as in step (3) of Synthesis 1).

Synthesis 6) Preparation of Resin-Cys(Trt)-Thr(tBu)-Asn (Trt)-Met-Leu-Trp(Boc)-Fmoc (SEQ ID NO: 5) (Synthesis of Poly 6mer)

Step (1): Preparation of Fmoc Deprotection

The target compound, Fmoc-deprotected resin-Cys(Trt)-Thr(tBu)-Asn(Trt)-Met-Leu (SEQ ID NO: 4), was obtained in the same manner as in step (1) of Synthesis 1) with the polypeptide (synthesis of poly 5mer) prepared in Synthesis 5).

Step (2): Activation of Trp(Boc)-Fmoc(W)

The target compound, Trp(Boc)-Fmoc, was activated in the same manner as in step (2) of Synthesis 1) with 26.1 g of Trp(Boc)-Fmoc.

Step (3): Preparation of Resin-Cys(Trt)-Thr(tBu)-Asn(Trt)-Met-Leu-Trp(Boc)-Fmoc (SEQ ID NO: 5) (Synthesis of Poly 6mer)

The target compound, resin-Cys(Trt)-Thr(tBu)-Asn(Trt)-Met-Leu-Trp(Boc)-Fmoc (SEQ ID NO: 5), was obtained in the same manner as in step (3) of Synthesis 1).

Synthesis 7) Preparation of Resin-Cys(Trt)-Thr(tBu)-Asn (Trt)-Met-Leu-Trp(Boc)-Gln(Trt)-Fmoc (SEQ ID NO: 6) (Synthesis of Poly 7mer)

Step (1): Preparation of Fmoc Deprotection

The target compound, Fmoc-deprotected resin-Cys(Trt)-Thr(tBu)-Asn(Trt)-Met-Leu-Trp(Boc) (SEQ ID NO: 5), was obtained in the same manner as in step (1) of Synthesis 1) with the polypeptide (synthesis of poly 6mer) prepared in Synthesis 6).

Step (2): Activation of Gln(Trt)-Fmoc (Q)

The target compound, Gln(Trt)-Fmoc, was activated in the same manner as in step (2) of Synthesis 1) with 30.3 g of Gln(Trt)-Fmoc.

Step (3): Preparation of Resin-Cys(Trt)-Thr(tBu)-Asn(Trt)-Met-Leu-Trp(Boc)-Gln(Trt)-Fmoc (SEQ ID NO: 6) (Synthesis of Poly 7mer)

The target compound, resin-Cys(Trt)-Thr(tBu)-Asn(Trt)-Met-Leu-Trp(Boc)-Gln(Trt)-Fmoc (SEQ ID NO: 6), was obtained in the same manner as in step (3) of Synthesis 1).

Synthesis 8) Preparation of Resin-Cys(Trt)-Thr(tBu)-Asn (Trt)-Met-Leu-Trp(Boc)-Gln(Trt)-Val-Fmoc (SEQ ID NO: 7) (Synthesis of Poly 8mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt) (SEQ ID NO: 6), was obtained in the same manner as in step (1) of Synthesis 1) with the polypeptide (synthesis of poly 7mer) prepared in Synthesis 7).

Step (2): Activation of Val-Fmoc(V)

The target compound, Val-Fmoc, was activated in the same manner as in step (2) of Synthesis 1) with 16.8 g of Val-Fmoc.

Step (3): Preparation of Resin-Cys(Trt)-Thr(tBu)-Asn(Trt)-Met-Leu-Trp(Boc)-Gln(Trt)-Val-Fmoc (SEQ ID NO: 7) (Synthesis of Poly 8mer)

The target compound, resin-Cys(Trt)-Thr(tBu)-Asn(Trt)-Met-Leu-Trp(Boc)-Gln(Trt)-Val-Fmoc, (SEQ ID NO: 7) was obtained in the same manner as in step (3) of Synthesis 1).

Synthesis 9) Preparation of Resin-Cys(Trt)-Thr(tBu)-Asn (Trt)-Met-Leu-Trp(Boc)-Gln(Trt)-Val-Phe-Fmoc (SEQ ID NO: 8) (Synthesis of Poly 9mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val, (SEQ ID NO: 7) was obtained in the same manner as in step (1) of Synthesis 1) with the polypeptide (synthesis of poly 8mer) prepared in Synthesis 8).

Step (2): Activation of Phe-Fmoc(F)

The target compound, Phe-Fmoc, was activated in the same manner as in step (2) of Synthesis 1) with 19.2 g of Phe-Fmoc.

Step (3): Preparation of Resin-Cys(Trt)-Thr(tBu)-Asn(Trt)-Met-Leu-Trp(Boc)-Gln(Trt)-Val-Phe-Fmoc (SEQ ID NO: 8) (Synthesis of Poly 9mer)

The target compound, resin-Cys(Trt)-Thr(tBu)-Asn(Trt)-Met-Leu-Trp(Boc)-Gln(Trt)-Val-Phe-Fmoc (SEQ ID NO: 8), was obtained in the same manner as in step (3) of Synthesis 1).

Synthesis 10) Preparation of Resin-Cys(Trt)-Thr(tBu)-Asn (Trt)-Met-Leu-Trp(Boc)-Gln(Trt)-Val-Phe-Fmoc (SEQ ID NO: 8) (Synthesis of Poly 10mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe (SEQ ID NO: 8), was obtained in the same manner as in step (1) of Synthesis 1) with the polypeptide (synthesis of poly 9mer) prepared in Synthesis 9).

Step (2): Activation of Glu(OtBu)-Fmoc(E)

The target compound, Glu(OtBu)-Fmoc, was activated in the same manner as in step (2) of Synthesis 1) with 21.1 g of Glu(OtBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Fmoc (SEQ ID NO: 9) (Synthesis of Poly 10mer)

The target compound, resin-Cys(Trt)-Thr(tBu)-Asn(Trt)-Met-Leu-Trp(Boc)-Gln(Trt)-Val-Phe-Glu(OtBu)-Fmoc (SEQ ID NO: 9), was obtained in the same manner as in step (3) of Synthesis 1).

Synthesis 11) Preparation of Resin-Cys(Trt)-Thr(tBu)-Asn (Trt)-Met-Leu-Trp(Boc)-Gln(Trt)-Val-Phe-Glu(OtBu)-Lys (Alloc)-Fmoc (SEQ ID NO: 10) (Synthesis of Poly 11mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu) (SEQ ID NO: 9), was obtained in the same manner as in step (1) of Synthesis 1) with the polypeptide (synthesis of poly 10mer) prepared in Synthesis 10).

Step (2): Activation of Lys(Alloc)-Fmoc(K)

The target compound, Lys(Alloc)-Fmoc, was activated in the same manner as in step (2) of Synthesis 1) with 22.4 g of Lys(Alloc)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Fmoc (SEQ ID NO: 10) (Synthesis of Poly 11mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Fmoc (SEQ ID NO: 10), was obtained in the same manner as in step (3) of Synthesis 1).

Synthesis 12) Preparation of Resin-Cys(Trt)-Thr(tBu)-Asn (Trt)-Met-Leu-Trp(Boc)-Gln(Trt)-Val-Phe-Glu(OtBu)-Lys (Alloc)-Ala-Fmoc (SEQ ID NO: 11) (Synthesis of Poly 12mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc) (SEQ ID NO: 10), was obtained in the same manner as in step (1) of Synthesis 1) with the polypeptide (synthesis of poly 11mer) prepared in Synthesis 11).

Step (2): Activation of Ala-Fmoc (A)

The target compound, Ala-Fmoc, was activated in the same manner as in step (2) of Synthesis 1) with 15.4 g of Ala-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Fmoc (SEQ ID NO: 11) (Synthesis of Poly 12mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Fmoc (SEQ ID NO: 11), was obtained in the same manner as in step (3) of Synthesis 1).

Synthesis 13) Preparation of Resin-Cys(Trt)-Thr(tBu)-Asn (Trt)-Met-Leu-Trp(Boc)-Gln(Trt)-Val-Phe-Glu(OtBu)-Lys (Alloc)-Ala-Arg(Pbf)-Fmoc (SEQ ID NO: 12) (Synthesis of Poly 13mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala (SEQ ID NO: 11), was obtained in the same manner as in step (1) of Synthesis 1) with the polypeptide (synthesis of poly 12mer) prepared in Synthesis 12).

Step (2): Activation of Arg(Pbf)-Fmoc (R)

The target compound, Arg(Pbf)-Fmoc, was activated in the same manner as in step (2) of Synthesis 1) with 32.2 g of Arg(Pbf)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Fmoc (SEQ ID NO: 12) (Synthesis of Poly 13mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Fmoc (SEQ ID NO: 12), was obtained in the same manner as in step (3) of Synthesis 1).

Synthesis 14) Preparation of Resin-Cys(Trt)-Thr(tBu)-Asn (Trt)-Met-Leu-Trp(Boc)-Gln(Trt)-Val-Phe-Glu(OtBu)-Lys (Alloc)-Ala-Arg(Pbf)-Lys(Boc)-Fmoc (SEQ ID NO: 13) (Synthesis of Poly 14mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf) (SEQ ID NO: 12), was obtained in the same manner as in step (1) of Synthesis 1) with the polypeptide (synthesis of poly 13mer) prepared in Synthesis 13).

Step (2): Activation of Lys(Boc)-Fmoc(K)

The target compound, Lys(Boc)-Fmoc, was activated in the same manner as in step (2) of Synthesis 1) with 23.2 g of Lys(Boc)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Fmoc (SEQ ID NO: 13) (Synthesis of Poly 14mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Fmoc (SEQ ID NO: 13), was obtained in the same manner as in step (3) of Synthesis 1).

Synthesis 15) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Fmoc (SEQ ID NO: 14) (Synthesis of Poly 15mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc) (SEQ ID NO: 13), was obtained in the same manner as in step (1) of Synthesis 1) with the polypeptide (synthesis of poly 14mer) prepared in Synthesis 14).

Step (2): Activation of Glu(OAll)-Fmoc(E)

The target compound, Glu(OAll)-Fmoc, was activated in the same manner as in step (2) of Synthesis 1) with 20.3 g of Glu(OAll)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Fmoc (SEQ ID NO: 14) (Synthesis of Poly 15mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Fmoc (SEQ ID NO: 14), was obtained in the same manner as in step (3) of Synthesis 1).

Synthesis 16) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Fmoc (SEQ ID NO: 15) (Synthesis of Poly 16mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll) (SEQ ID NO: 14), was obtained in the same manner as in step (1) of Synthesis 1) with the polypeptide (synthesis of poly 15mer) prepared in Synthesis 15).

Step (2): Activation of Asp(OtBu)-Fmoc(D)

The target compound, Asp(OtBu)-Fmoc, was activated in the same manner as in step (2) of Synthesis 1) with 20.4 g of Asp(OtBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Fmoc (SEQ ID NO: 15) (Synthesis of Poly 16mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Fmoc (SEQ ID NO: 15), was obtained in the same manner as in step (3) of Synthesis 1).

Synthesis 17) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Fmoc (SEQ ID NO: 16) (Synthesis of Poly 17mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu) (SEQ ID NO: 15), was obtained in the same manner as in step (1) of Synthesis 1) with the polypeptide (synthesis of poly 16mer) prepared in Synthesis 16).

Step (2): Activation of Leu-Fmoc (L)

The target compound, Leu-Fmoc, was activated in the same manner as in step (2) of Synthesis 1) with 17.5 g of Leu-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Fmoc (SEQ ID NO: 16) (Synthesis of Poly 17mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Fmoc (SEQ ID NO: 16), was obtained in the same manner as in step (3) of Synthesis 1).

Synthesis 18) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Fmoc (SEQ ID NO: 17) (Synthesis of Poly 18mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu (SEQ ID NO: 16), was obtained in the same manner as in step (1) of Synthesis 1) with the polypeptide (synthesis of poly 17mer) prepared in Synthesis 17).

Step (2): Activation of Tyr(tBu)-Fmoc (Y)

The target compound, Tyr(tBu)-Fmoc, was activated in the same manner as in step (2) of Synthesis 1) with 22.8 g of Tyr(tBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Fmoc (SEQ ID NO: 17) (Synthesis of Poly 18mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Fmoc (SEQ ID NO: 17), was obtained in the same manner as in step (3) of Synthesis 1).

Synthesis 19) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Fmoc (SEQ ID NO: 18) (Synthesis of Poly 19mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu) (SEQ ID NO: 17), was obtained in the same manner as in step (1) of Synthesis 1) with the polypeptide (synthesis of poly 18mer) prepared in Synthesis 18).

Step (2): Activation of Lys(Boc)-Fmoc(K)

The target compound, Lys(Boc)-Fmoc, was activated in the same manner as in step (2) of Synthesis 1) with 23.2 g of Lys(Boc)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Fmoc (SEQ ID NO: 18) (Synthesis of Poly 19mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Fmoc (SEQ ID NO: 18), was obtained in the same manner as in step (3) of Synthesis 1).

Synthesis 20) Preparation of Resin-Cys(Trt)-Thr(tBu)-Asn(Trt)-Met-Leu-Trp(Boc)-Gln(Trt)-Val-Phe-Glu(OtBu)-Lys (Alloc)-Ala-Arg(Pbf)-Lys(Boc)-Glu(OAll)-Asp(OtBu)-Leu-Tyr(tBu)-Lys(Boc)-Ser(tBu)-Fmoc (SEQ ID NO: 19) (Synthesis of Poly 20mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc) (SEQ ID NO: 18), was obtained in the same manner as in step (1) of Synthesis 1) with the polypeptide (synthesis of poly 19mer) prepared in Synthesis 19).

Step (2): Activation of Ser(tBu)-Fmoc(S)

The target compound, Ser(tBu)-Fmoc, was activated in the same manner as in step (2) of Synthesis 1) with 19.0 g of Ser(tBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Fmoc (SEQ ID NO: 19) (Synthesis of Poly 20mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Fmoc (SEQ ID NO: 19), was obtained in the same manner as in step (3) of Synthesis 1).

Synthesis 21) Preparation of Resin-Cys(Trt)-Thr(tBu)-Asn(Trt)-Met-Leu-Trp(Boc)-Gln(Trt)-Val-Phe-Glu(OtBu)-Lys-Ala-Arg(Pbf)-Lys(Boc)-Glu-Asp(OtBu)-Leu-Tyr(tBu)-Lys(Boc)-Ser(tBu)-Tyr(tBu)-Fmoc (SEQ ID NO: 47) (Synthesis of Poly 21mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu) (SEQ ID NO: 19), was obtained in the same manner as in step (1) of Synthesis 1) with the polypeptide (synthesis of poly 20mer) prepared in Synthesis 20).

Step (2): Activation of Tyr(tBu)-Fmoc(Y)

The target compound, Tyr(tBu)-Fmoc, was activated in the same manner as in step (2) of Synthesis 1) with 22.8 g of Tyr(tBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Fmoc (SEQ ID NO: 20) (Synthesis of Poly 21mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Fmoc (SEQ ID NO: 20), was obtained in the same manner as in step (3) of Synthesis 1).

Synthesis 22) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Fmoc (SEQ ID NO: 21) (Synthesis of Poly 22mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu) (SEQ ID NO: 20), was obtained in the same manner as in step (1) of Synthesis 1) with the polypeptide (synthesis of poly 21mer) prepared in Synthesis 21).

Step (2): Activation of Asp(OtBu)-Fmoc(D)

The target compound, Asp(OtBu)-Fmoc, was activated in the same manner as in step (2) of Synthesis 1) with 20.4 g of Asp(OtBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Fmoc (SEQ ID NO: 21) (Synthesis of Poly 22mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Fmoc (SEQ ID NO: 21), was obtained in the same manner as in step (3) of Synthesis 1).

Synthesis 23) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Fmoc (SEQ ID NO: 22) (Synthesis of Poly 23mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu) (SEQ ID NO: 21), was obtained in the same manner as in step (1) of Synthesis 1) with the polypeptide (synthesis of poly 22mer) prepared in Synthesis 22).

Step (2): Activation of Ser(tBu)-Fmoc(S)

The target compound, Ser(tBu)-Fmoc, was activated in the same manner as in step (2) of Synthesis 1) with 19.0 g of Ser(tBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Fmoc (SEQ ID NO: 22) (Synthesis of Poly 23mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Fmoc (SEQ ID NO: 22), was obtained in the same manner as in step (3) of Synthesis 1).

Synthesis 24) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Fmoc (SEQ ID NO: 23) (Synthesis of Poly 24mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu) (SEQ ID NO: 22), was obtained in the same manner as in step (1) of Synthesis 1) with the polypeptide (synthesis of poly 23mer) prepared in Synthesis 23).

Step (2): Activation of Thr(tBu)-Fmoc(T)

The target compound, Thr(tBu)-Fmoc, was activated in the same manner as in step (2) of Synthesis 1) with 19.7 g of Thr(tBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu) Fmoc (SEQ ID NO: 23) (Synthesis of Poly 24mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Thr(tBu) Fmoc (SEQ ID NO: 23), was obtained in the same manner as in step (3) of Synthesis 1).

Synthesis 25) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Fmoc (SEQ ID NO: 24) (Synthesis of Poly 25mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)- Ser(tBu)-Thr(tBu) (SEQ ID NO: 23), was obtained in the same manner as in step (1) of Synthesis 1) with the polypeptide (synthesis of poly 24mer) prepared in Synthesis 24).

Step (2): Activation of Phe-Fmoc(F)

The target compound, Phe-Fmoc, was activated in the same manner as in step (2) of Synthesis 1) with 19.2 g of Phe-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Fmoc (SEQ ID NO: 24) (Synthesis of Poly 25mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Thr(tBu)-Phe- Fmoc (SEQ ID NO: 24), was obtained in the same manner as in step (3) of Synthesis 1).

Synthesis 26) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Fmoc (SEQ ID NO: 25) (Synthesis of Poly 26mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)- Ser(tBu)-Thr(tBu)-Phe (SEQ ID NO: 24), was obtained in the same manner as in step (1) of Synthesis 1) with the polypeptide (synthesis of poly 25mer) prepared in Synthesis 25).

Step (2): Activation of Thr(tBu)-Fmoc(T)

The target compound, Thr(tBu)-Fmoc, was activated in the same manner as in step (2) of Synthesis 1) with 19.7 g of Thr(tBu)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Fmoc (SEQ ID NO: 25) (Synthesis of Poly 26mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Thr(tBu)-Phe- Thr(tBu)-Fmoc (SEQ ID NO: 25), was obtained in the same manner as in step (3) of Synthesis 1).

Synthesis 27) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Gly-Fmoc (SEQ ID NO: 26) (Synthesis of Poly 27mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-SertBu)-Tyr(tBu)-Asp(OtBu)-Ser(tBu)- Thr(tBu)-Phe-Thr(tBu) (SEQ ID NO: 48), was obtained in the same manner as in step (1) of Synthesis 1) with the polypeptide (synthesis of poly 26mer) prepared in Synthesis 26).

Step (2): Activation of Gly-Fmoc(G)

The target compound, Gly-Fmoc, was activated in the same manner as in step (2) of Synthesis 1) with 14.7 g of Gly-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Gly-Fmoc (SEQ ID NO: 26) (Synthesis of Poly 27mer)

The target compound, Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Thr(tBu)-Phe- Thr(tBu)-Gly-Fmoc (SEQ ID NO: 26), was obtained in the same manner as in step (3) of Synthesis 1).

Synthesis 28) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Gly-Gln(Trt)-Fmoc (SEQ ID NO: 27) (Synthesis of Cyclized Poly 28mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)- Ser(tBu)-Thr(tBu)-Phe-Thr(tBu)-Gly (SEQ ID NO: 26), was obtained in the same manner as in step (1) of Synthesis 1) with the polypeptide (synthesis of poly 27mer) prepared in Synthesis 27).

Step (2): Activation of Gln(Trt)-Fmoc(Q)

The target compound, Gln(Trt)-Fmoc, was activated in the same manner as in step (2) of Synthesis 1) with 30.3 g of Gln(Trt)-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Gly-Gln(Trt)-Fmoc (SEQ ID NO: 27) (Synthesis of Poly 28mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Thr(tBu)-Phe- Thr(tBu)-Gly-Gln(Trt)-Fmoc (SEQ ID NO: 27), was obtained in the same manner as in step (3) of Synthesis 1).

Synthesis 29) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Gly-Gln(Trt)-Aib-Fmoc (SEQ ID NO: 28) (Synthesis of Poly 29mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)- Ser(tBu)-Thr(tBu)-Phe-Thr(tBu)-Gly-Gln(Trt) (SEQ ID NO: 27), was obtained in the same manner as in step (1) of Synthesis 1) with the polypeptide (synthesis of poly 28mer) prepared in Synthesis 28).

Step (2): Activation of Aib-Fmoc

The target compound, Aib-Fmoc, was activated in the same manner as in step (2) of Synthesis 1) with 16.1 g of Aib-Fmoc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Gly-Gln(Trt)-Aib-Fmoc (SEQ ID NO: 28) (Synthesis of Poly 29mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Thr(tBu)-Phe- Thr(tBu)-Gly-Gln(Trt)-Aib-Fmoc (SEQ ID NO: 28), was obtained in the same manner as in step (3) of Synthesis 1).

Synthesis 30) Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Gly-Gln(Trt)-Aib-His(Trt)-Boc (SEQ ID NO: 29) (Synthesis of Poly 30mer)

Step (1): Preparation of Fmoc Deprotection

The target compound, Fmoc-deprotected resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)- Ser(tBu)-Thr(tBu)-Phe-Thr(tBu)-Gly-Gln(Trt)-Aib (SEQ ID NO: 28), was obtained in the same manner as in step (1) of Synthesis 1) with the polypeptide (synthesis of poly 29mer) prepared in Synthesis 29).

Step (2): Activation of His(Trt)-Boc(H)

The target compound, His(Trt)-Boc, was activated in the same manner as in step (2) of Synthesis 1) with 30.7 g of His(Trt)-Boc.

Step (3): Preparation of Resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)- Thr(tBu)-Phe-Thr(tBu)-Gly-Gln(Trt)-Aib-His(Trt)-Boc (SEQ ID NO: 29) (Synthesis of Poly 30mer)

The target compound, resin-Cys(Trt)-Thr(tBu)-Asn(Trt)-Met-Leu-Trp(Boc)-Gln(Trt)-Val-Phe-Glu(OtBu)-Lys(Alloc)-Ala-Arg(Pbf)-Lys(Boc)-Glu(OAll)-Asp(OtBu)-Leu-Tyr(tBu)-Lys(Boc)-Ser(tBu)-Tyr(tBu)-Asp(OtBu)-Ser(tBu)-Thr(tBu)-Phe- Thr(tBu)-Gly-Gln(Trt)-Aib-His(Trt)-Boc (SEQ ID NO: 29), was obtained in the same manner as in step (3) of Synthesis 1).

Comparative Example 3: Preparation of Cyclized Polypeptides

In a vessel, 11.5 g of tetrakispalladium and 800 mL of dichloromethane were added, and the mixture was completely dissolved by stirring. 78.6 mL of N-methylaniline and 38.5 mL of phenylsilane were added to the dissolved reaction solution and stirred for 5 minutes. 480 mL of dichloromethane was added to the polypeptide (synthesis of poly 30mer) prepared in Synthesis 30), stirred for 2 minutes, and then filtered. This process was performed three times. The thus-prepared reaction solution was added to the filtered resin, stirred at room temperature for 5 hours, and then filtered. 480 mL of dichloromethane was added to the filtered resin, stirred for 2 minutes, and then filtered. This process was performed five times. 480 mL of methanol was added to the filtered resin, stirred for 2 minutes, and then filtered. This process was performed twice.

Step (2): Preparation of Cyclized Polypeptide (Synthesis of Cyclized Poly 30mer)

In a vessel, 56.6 g of HATU and 480 mL of dimethylformamide were added, and the mixture was completely dissolved by stirring. 51.8 mL of N, N-diisopropylethylamine was added to the dissolved reaction solution and stirred at room temperature for 5 minutes. The thus-prepared reaction solution was added to the polypeptide (partially deprotected 30mer) prepared in step (1), stirred at room temperature for 3 hours, and then filtered. 480 mL of dimethylformamide was added to the filtered resin, stirred for 2 minutes, and then filtered. 480 mL of methanol was added to the filtered resin, stirred for 2 minutes, and then filtered. This process was performed three times. 480 mL of dimethylformamide was added to the filtered resin, stirred for 2 minutes, and then filtered. This process was performed three times. Through the process, the target compound, resin-Cys(Trt)-Thr(tBu)-Asn(Trt)-Met-Leu-Trp(Boc)-Gln(Trt)-Val-Phe-Glu(OtBu)-cyclo[Lys-Ala-Arg(Pbf)-Lys(Boc)-Glu]-Asp(OtBu)-Leu-Tyr(tBu)-Lys(Boc)-Ser(tBu)-Tyr(tBu)-Asp(OtBu)-Ser(tBu)-Thr(tBu)-Phe-Thr(tBu)-Gly-Gln(Trt)-Aib-His(Trt)-Boc (SEQ ID NO: 30), which is a cyclized polypeptide, was obtained.

Comparative Example 4: Preparation of $NH_2$-Cys-Thr-Asn-Met-Leu-Trp-Gln-Val-Phe-Glu-cyclo[Lys-Ala-Arg-Lys-Glu]-Asp-Leu-Tyr-Lys-Ser-Tyr-Asp-Ser-Thr-Phe-Thr-Gly-Gln-Aib-His-H (SEQ ID NO: 32). TFA (Cleavage of Protecting Groups and Resins)

The target compound, $NH_2$-Cys-Thr-Asn-Met-Leu-Trp-Gln-Val-Phe-Glu-cyclo[Lys-Ala-Arg-Lys-Glu]-Asp-Leu-Tyr-Lys-Ser-Tyr-Asp-Ser-Thr-Phe-Thr-Gly-Gln-Aib-His-H (SEQ ID NO: 32)· TFA was obtained in the same manner as in Example 4.

TABLE 1

| | Chromatogram Area (%) | |
|---|---|---|
| | Example | Comparative Example |
| Specific gravity of maximum single related substance (%) | 14.4 | 28.6 |
| Crude purity (%) | 61.6 | 18.0 |
| Final yield after purification (%) | 15 | 2 |

In the chromatogram of FIG. 1, the box indicates the peak of the main product, the arrow indicates the peak position of the maximum single related substance, and the blue circle indicates the chromatogram area where the peak corresponding to the maximum single related substance of Comparative Example appears. The relative retention time (RRT) of each peak is as follows.

Main Product: 1.03 to 1.21

Maximum Single Related Substance of Examples: 0.86

Maximum Single Related Substance of Comparative Examples: 1.12

TABLE 2

| Purity of each step of production process | | | |
|---|---|---|---|
| Example | 1~15 mer purity after linear synthesis: 79.0% | 1~15 mer purity after cyclization process: 75.0% | 16~30 mer purity of linear synthesis after cyclization: 61.6% |
| Comparaitve Example | 1~30 mer purity after linear synthesis: 60.3% | | 1~30 mer purity after cyclization process: 18.0% |

As can be seen from the results summarized in Tables 1 and 2, the Example according to the present invention showed a much improved result (improved by about 7.5 times) compared to the Comparative Example of the prior art in which cyclization was performed after linear synthesis. In addition, it was confirmed that the specific gravity of related substances in the process was reduced by half relative to the maximum single related substance (see ratio and crude purity of maximum single related substances of Table 1). In terms of the types of the maximum single related substances, the maximum single related substance of the Comparative Example had an RRT of 1.12, but the related substance of the Example had an RRT of 0.86, which was further away from the main product peak (marked in the box of FIG. 1) in the chromatogram, and changed to a material which could be easily separated. The amount of impurities around the main product (RRT 1.03 to 1.21) where the peak of the maximum single related compound of the Comparative Example was detected, which was relatively difficult to separate, was significantly reduced in the Example (circle in FIG. 1), and thus, the final purification process was simplified, and the loss rate of the final purification process was greatly improved by about 2.2 times (see crude purity and final yield after purification of Table 1).

The invention claimed is:

1. A peptide intermediate compound represented by Chemical Formula 1 below:

[Chemical Formula 1]

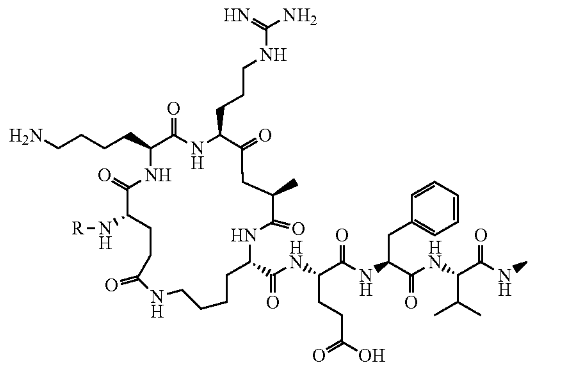

-continued

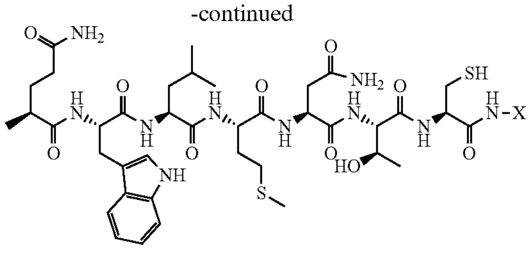

R-cyclo (Glu-Lys-Arg-Ala-Lys)-Glu-Phe-Val-Gln-Trp-Leu-Met-Asn-Thr-Cys-X (SEQ ID NO: 1):

wherein, R is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; X is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; and these substituents may be further substituted with one or more identical or different substituents selected from the group consisting of H, halogen, cyano, linear or branched $C_{1-6}$ alkyl, linear or branched $C_{2-10}$ alkenyl, $C_{3-10}$ cycloalkyl, halo $C_{1-5}$ alkyl, hydroxy $C_{1-6}$ alkyl, amino, mono or di $C_{1-6}$ alkylamino, oxo, hydroxy, $C_{1-6}$ alkoxy, $C_{6-12}$ arylsulfonyl, and $C_{1-6}$ alkylsulfonyl.

2. The peptide intermediate compound of claim 1, wherein R is selected from the group consisting of H, linear or branched $C_{1-12}$ alkyloxy, $C_{6-12}$ aryloxy, and $C_{1-6}$ alkyl $C_{6-12}$ aryloxy.

3. The peptide intermediate compound of claim 2, wherein R is tert-butyloxy or 9-fluorenylmethyloxy.

4. The peptide intermediate compound of claim 1, wherein R is H, and X is H.

5. A resin composite compound represented by Chemical Formula 3 below:

[Chemical Formula 3]

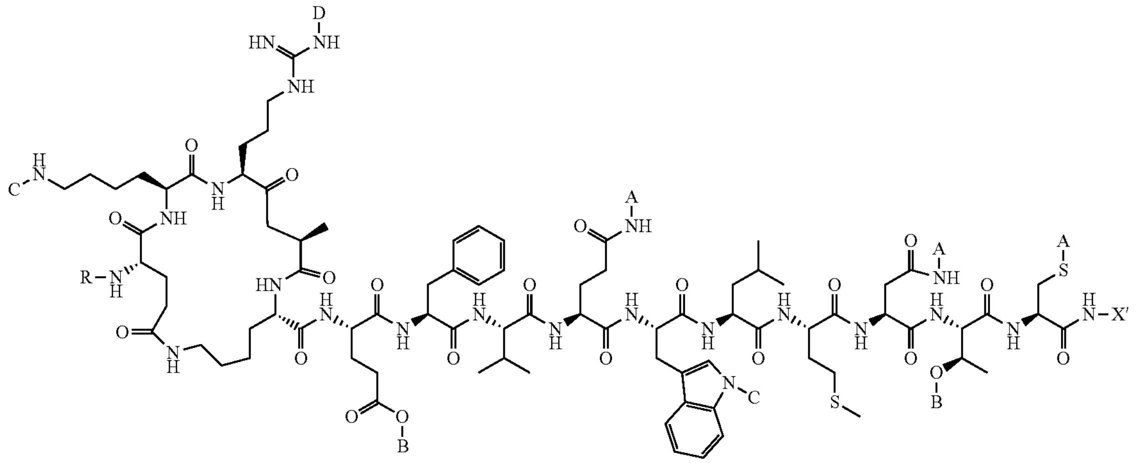

wherein A to D are protecting groups; A to D are each independently selected from the group consisting of triphenylmethyl (Trt), tert-butyl (tBu), t-butyloxycarbonyl (Boc), and 2,2,4,6,7-pentamethyldihydrobenzofuran-5-sulfonyl (Pbf); R is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; X' is a resin; and these substituents may be further substituted with one or more identical or different substituents selected from the group consisting of H, halogen, cyano, linear or branched $C_{1-6}$ alkyl, linear or branched $C_{2-10}$ alkenyl, $C_{3-10}$ cycloalkyl, halo $C_{1-5}$ alkyl, hydroxy $C_{1-6}$ alkyl, amino, mono or di $C_{1-6}$ alkylamino, oxo, hydroxy, $C_{1-6}$ alkoxy, $C_{6-12}$ arylsulfonyl, and $C_{1-6}$ alkylsulfonyl.

6. The resin composite compound of claim 5, wherein a resin of the resin composite compound is a polystyrene (PS)-based resin or a polystyrene-polyethylene glycol copolymer (PS-PEG copolymer)-based resin.

7. The resin composite compound of claim 5, wherein the resin is a Rink amide resin.

8. A method for preparing a resin composite compound represented by Chemical Formula 3 below, comprising the steps of:

(1) swelling a resin in a polar aprotic solvent to give a deprotected resin;

(2) coupling by adding an activated protected amino acid to the deprotected resin in a reactor;

(3) repeating step (2) until a peptide comprising the amino acid sequence of SEQ ID NO: 1 is formed to give a synthesized peptide;

(4) preparing a partially deprotected resin by reacting the synthesized peptide of step (3) with tetrakispalladium, N-methylaniline, and phenylsilane in a solvent; and (5) cyclizing the synthesized peptide obtained in step (4) by adding a coupling reagent in a polar aprotic solvent:

[Chemical Formula 3]

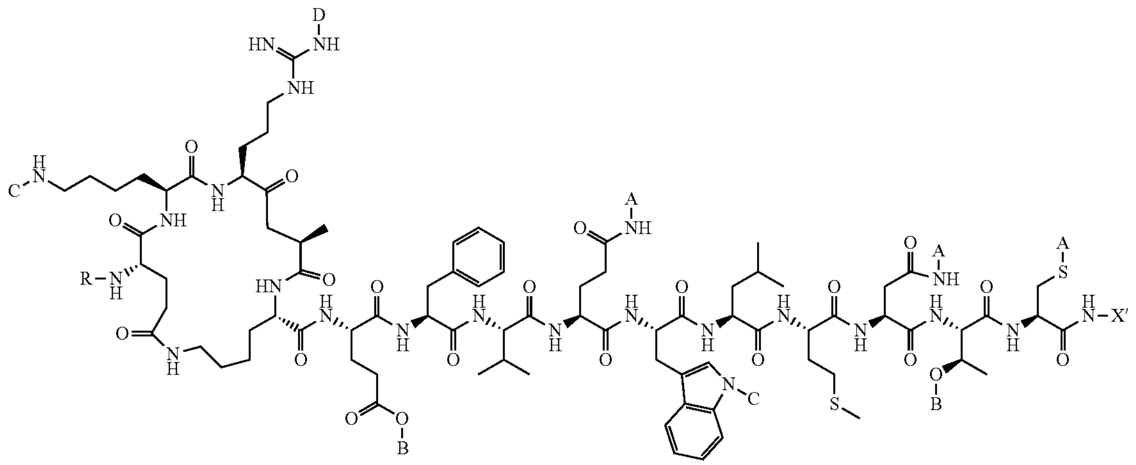

wherein A to D are protecting groups; A to D are each independently selected from the group consisting of triphenylmethyl (Trt), tert-butyl (tBu), t-butyloxycarbonyl (Boc), and 2,2,4,6,7-pentamethyldihydrobenzofuran-5-sulfonyl (Pbf); R is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; X' is a resin; and these substituents may be further substituted with one or more identical or different substituents selected from the group consisting of H, halogen, cyano, linear or branched $C_{1-6}$ alkyl, linear or branched $C_{2-10}$ alkenyl, $C_{3-10}$ cycloalkyl, halo $C_{1-5}$ alkyl, hydroxy $C_{1-6}$ alkyl, amino, mono or di $C_{1-6}$ alkylamino, oxo, hydroxy, $C_{1-6}$ alkoxy, $C_{6-12}$ arylsulfonyl, and $C_{1-6}$ alkylsulfonyl.

9. The method of claim 8, wherein the polar aprotic solvent in step (1) and step (5) is selected from the group consisting of dimethylformamide, dimethylacetamide, and mixtures thereof.

10. The method of claim 8, wherein the solvent in step (4) is selected from the group consisting of dichloromethane, chloroform, and mixtures thereof.

11. The method of claim 8, wherein the coupling reagent in step (5) is selected from 1-hydroxy-1H-benzotriazole/1,3-diisopropylcarbodiimide or HATU (1-[bis(dimethylamino)methylene]-1H-1,2,3-triazolo[4,5-b]pyridinium 3-oxide hexafluorophosphate)/N,N-diisopropylethylamine.

12. A method for preparing a physiologically active polypeptide represented by Chemical Formula 2 below or a pharmaceutically acceptable salt thereof, comprising:

(1) a reaction step of obtaining a peptide-resin composite by reacting the resin composite compound of Chemical Formula 3 below with amino acids to form a physiologically active polypeptide of Chemical Formula 2; and

[Chemical Formula 3]

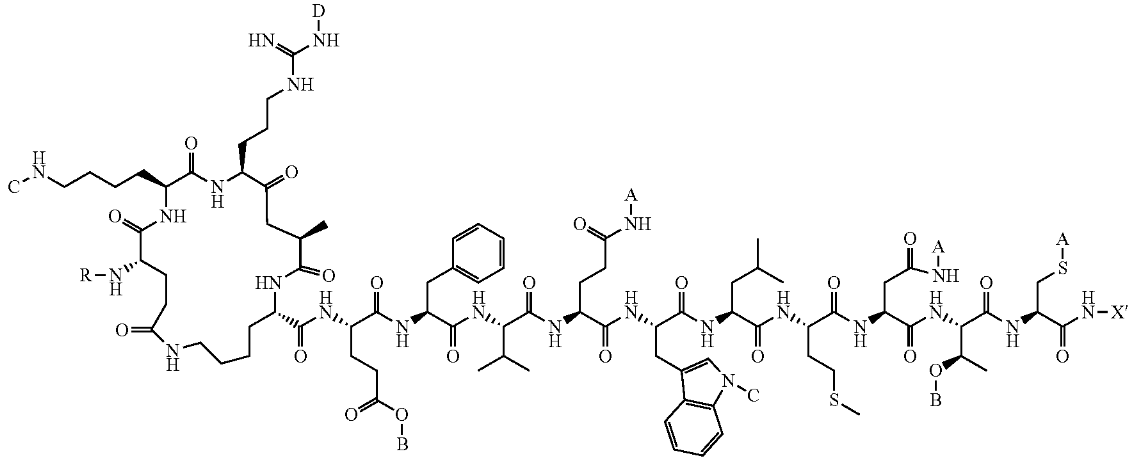

wherein A to D are protecting groups; A to D are each independently selected from the group consisting of triphenylmethyl (Trt), tert-butyl (tBu), t-butyloxycarbonyl (Boc), and 2,2,4,6,7-pentamethyldihydrobenzofuran-5-sulfonyl (Pbf); R is selected from the group consisting of H, linear or branched $C_{1-12}$ alkyl, linear or branched $C_{1-12}$ alkyloxycarbonyl, linear or branched $C_{2-12}$ alkenyl, $C_{3-10}$ cycloalkyl, heterocycloalkyl, $C_{6-12}$ aryl, $C_{6-12}$ aryloxycarbonyl, $C_{1-6}$ alkyl $C_{6-12}$ aryl, $C_{1-6}$ alkyl $C_{6-12}$ aryloxycarbonyl, and heteroaryl; X' is a resin; and these substituents may be further substituted with one or more identical or different substituents selected from the group consisting of H, halogen, cyano, linear or branched $C_{1-6}$ alkyl, linear or branched $C_{2-10}$ alkenyl, $C_{3-10}$ cycloalkyl, halo $C_{1-5}$ alkyl, hydroxy $C_{1-6}$ alkyl, amino, mono or di $C_{1-6}$ alkylamino, oxo, hydroxy, $C_{1-6}$ alkoxy, $C_{6-12}$ arylsulfonyl, and $C_{1-6}$ alkylsulfonyl

[Chemical Formula 2]
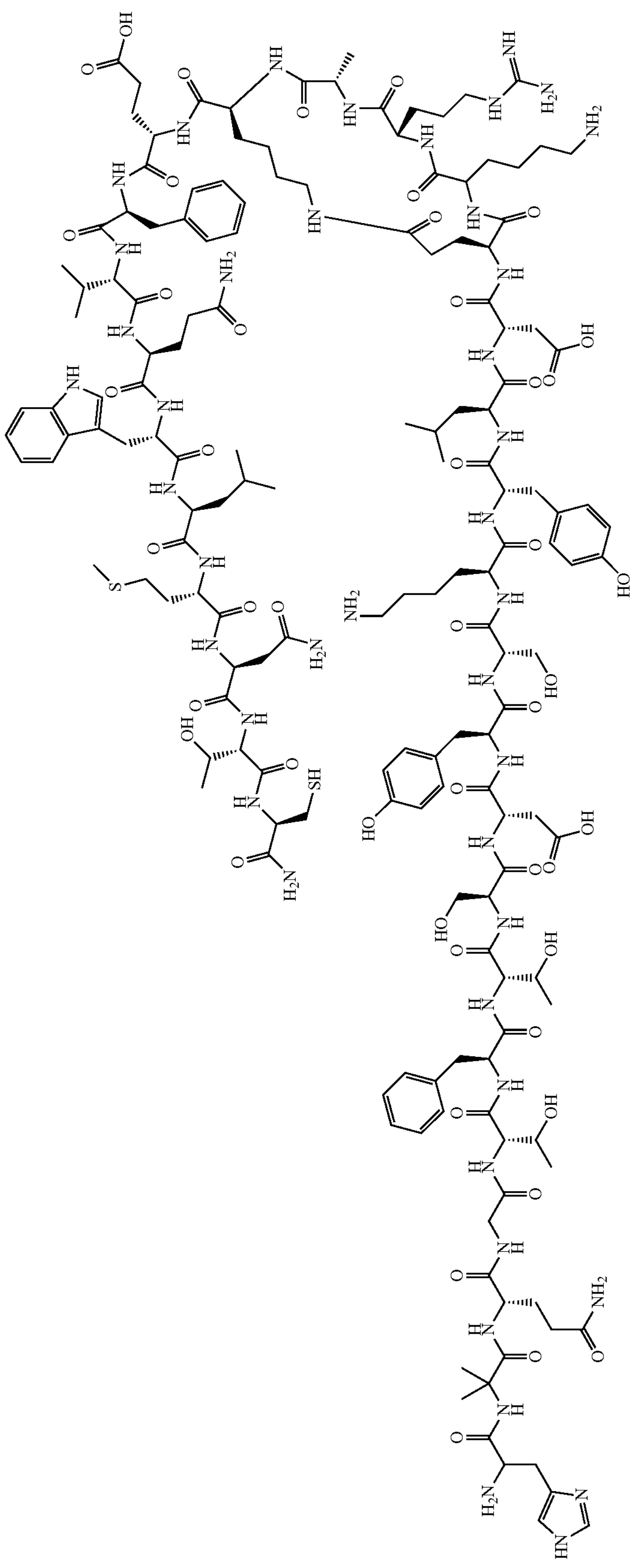

H-His-Aib-Gln-Gly-Thr-Phe-Thr-Ser-Asp-Tyr-Ser-Lys-Tyr-Leu-Asp-cyclo (Glu-Lys-Arg-Ala-Lys) Glu-Phe-Val-Gln-Trp-Leu-Met-Asn-Thr-Cys-$NH_2$ (SEQ ID NO: 2)

(2) a cleavage step of cleaving the physiologically active polypeptide of Chemical Formula 2 from the peptide-resin composite.

13. The method of claim 12, wherein the reaction step comprises deprotecting the peptide-resin composite in a polar aprotic solvent, wherein the polar aprotic solvent is selected from the group consisting of dimethylformamide, dimethylacetamide, and mixtures thereof.

14. The method of claim 12, wherein the cleavage step is carried out in a medium containing a solution of trifluoroacetic acid, at least one scavenger, and dichloromethane.

15. The method of claim 14, wherein the scavenger is selected from the group consisting of triisopropylsilane, triethylsilane, phenol, anisole, thioanisole, water, ethanedithiol, 1-dodecanethiol, dithiothreitol, and indole.

16. The method of claim 12, wherein the pharmaceutically acceptable salt is trifluoroacetate or acetate.

17. The method of claim 12, wherein the resin composite compound of Chemical Formula 3 is a Rink amide resin composite compound.

* * * * *

SEQUENCE LISTING

```
<160> NUMBER OF SEQ ID NOS: 49

<210> SEQ ID NO 1
<211> LENGTH: 15
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MISC_FEATURE
<222> LOCATION: (1)..(5)
<223> OTHER INFORMATION: Peptide is circular

<400> SEQUENCE: 1

Glu Lys Arg Ala Lys Glu Phe Val Gln Trp Leu Met Asn Thr Cys
1               5                   10                  15


<210> SEQ ID NO 2
<211> LENGTH: 30
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (19)..(23)
<223> OTHER INFORMATION: Peptide is circular

<400> SEQUENCE: 2

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30


<210> SEQ ID NO 3
<211> LENGTH: 4
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
```

-continued

<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)

<400> SEQUENCE: 3

Cys Thr Asn Met
1

<210> SEQ ID NO 4
<211> LENGTH: 5
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)

<400> SEQUENCE: 4

Cys Thr Asn Met Leu
1               5

<210> SEQ ID NO 5
<211> LENGTH: 6
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)

<400> SEQUENCE: 5

Cys Thr Asn Met Leu Trp
1               5

<210> SEQ ID NO 6
<211> LENGTH: 7
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)

<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)

<400> SEQUENCE: 6

Cys Thr Asn Met Leu Trp Gln
1               5

<210> SEQ ID NO 7
<211> LENGTH: 8
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)

<400> SEQUENCE: 7

Cys Thr Asn Met Leu Trp Gln Val
1               5

<210> SEQ ID NO 8
<211> LENGTH: 9
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)

<220> FEATURE:
<221> NAME/KEY: MOD_RES
<222> LOCATION: (7)..(7)
<223> OTHER INFORMATION: Gln(triphenylmethyl)

<400> SEQUENCE: 8

Cys Thr Asn Met Leu Trp Gln Val Phe
1 5

<210> SEQ ID NO 9
<211> LENGTH: 10
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)

<400> SEQUENCE: 9

Cys Thr Asn Met Leu Trp Gln Val Phe Glu
1 5 10

<210> SEQ ID NO 10
<211> LENGTH: 11
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:

```
<221> NAME/KEY: MOD_RES
<222> LOCATION: (11)..(11)
<223> OTHER INFORMATION: Lys((2-Propen-1-yl) carbonyl or Allyloxy
      carbonyl)

<400> SEQUENCE: 10

Cys Thr Asn Met Leu Trp Gln Val Phe Glu Lys
1               5                   10


<210> SEQ ID NO 11
<211> LENGTH: 12
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
      carbonyl)

<400> SEQUENCE: 11

Cys Thr Asn Met Leu Trp Gln Val Phe Glu Lys Ala
1               5                   10


<210> SEQ ID NO 12
<211> LENGTH: 13
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
```

<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)

<400> SEQUENCE: 12

Cys Thr Asn Met Leu Trp Gln Val Phe Glu Lys Ala Arg
1 5 10

<210> SEQ ID NO 13
<211> LENGTH: 14
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)

<400> SEQUENCE: 13

Cys Thr Asn Met Leu Trp Gln Val Phe Glu Lys Ala Arg Lys
1 5 10

<210> SEQ ID NO 14
<211> LENGTH: 15
<212> TYPE: PRT
<213> ORGANISM: Artificial Sequence
<220> FEATURE:
<223> OTHER INFORMATION: The sequence is artificially synthesized
<220> FEATURE:

-continued

<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (15)..(15)
<223> OTHER INFORMATION: Glu( 2-Propen-1-yl or allyl)

<400> SEQUENCE: 14

Cys Thr Asn Met Leu Trp Gln Val Phe Glu Lys Ala Arg Lys Glu
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:

<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu( 2-Propen-1-yl or allyl)
<220> FEATURE:
<221> NAME/KEY: MOD_RES
<222> LOCATION: (16)..(16)
<223> OTHER INFORMATION: Asp(tert-Butoxy)

<400> SEQUENCE: 15

Cys Thr Asn Met Leu Trp Gln Val Phe Glu Lys Ala Arg Lys Glu Asp
1 5 10 15

<210> SEQ ID NO 16
<211> LENGTH: 17
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (15)..(15)
<223> OTHER INFORMATION: Glu(2-Propen-1-yl or allyl)
<220> FEATURE:
<221> NAME/KEY: MOD_RES
<222> LOCATION: (16)..(16)

<223> OTHER INFORMATION: Asp(tert-Butoxy)

<400> SEQUENCE: 16

Cys Thr Asn Met Leu Trp Gln Val Phe Glu Lys Ala Arg Lys Glu Asp
1 5 10 15

Leu

<210> SEQ ID NO 17
<211> LENGTH: 18
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (15)..(15)
<223> OTHER INFORMATION: Glu(2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)

<400> SEQUENCE: 17

Cys Thr Asn Met Leu Trp Gln Val Phe Glu Lys Ala Arg Lys Glu Asp
1 5 10 15

Leu Tyr

<210> SEQ ID NO 18
<211> LENGTH: 19
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu( 2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)

<400> SEQUENCE: 18

Cys Thr Asn Met Leu Trp Gln Val Phe Glu Lys Ala Arg Lys Glu Asp
1               5                   10                  15

Leu Tyr Lys

<210> SEQ ID NO 19
<211> LENGTH: 20
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)

```
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl))
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
      carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu( 2-Propen-1-yl  or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)

<400> SEQUENCE: 19

Cys Thr Asn Met Leu Trp Gln Val Phe Glu Lys Ala Arg Lys Glu Asp
1               5                   10                  15

Leu Tyr Lys Ser
            20


<210> SEQ ID NO 20
<211> LENGTH: 21
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
```

<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu( 2-Propen-1-yl  or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)

<400> SEQUENCE: 20

```
Cys Thr Asn Met Leu Trp Gln Val Phe Glu Lys Ala Arg Lys Glu Asp
1               5                   10                  15

Leu Tyr Lys Ser Tyr
            20
```

<210> SEQ ID NO 21
<211> LENGTH: 22
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu( 2-Propen-1-yl  or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)

<400> SEQUENCE: 21

```
Cys Thr Asn Met Leu Trp Gln Val Phe Glu Lys Ala Arg Lys Glu Asp
1               5                   10                  15

Leu Tyr Lys Ser Tyr Asp
            20
```

<210> SEQ ID NO 22
<211> LENGTH: 23
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)

<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu( 2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)

<400> SEQUENCE: 22

```
Cys Thr Asn Met Leu Trp Gln Val Phe Glu Lys Ala Arg Lys Glu Asp
1               5                   10                  15

Leu Tyr Lys Ser Tyr Asp Ser
            20
```

<210> SEQ ID NO 23
<211> LENGTH: 24
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)

<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu( 2-Propen-1-yl  or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)

<400> SEQUENCE: 23

```
Cys Thr Asn Met Leu Trp Gln Val Phe Glu Lys Ala Arg Lys Glu Asp
1               5                   10                  15

Leu Tyr Lys Ser Tyr Asp Ser Thr
            20
```

```
<210> SEQ ID NO 24
<211> LENGTH: 25
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
      carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu(2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
```

<222> LOCATION: (24)..(24)
<223> OTHER INFORMATION: Thr(tert-butyl)

<400> SEQUENCE: 24

Cys Thr Asn Met Leu Trp Gln Val Phe Glu Lys Ala Arg Lys Glu Asp
1               5                   10                  15

Leu Tyr Lys Ser Tyr Asp Ser Thr Phe
            20                  25

<210> SEQ ID NO 25
<211> LENGTH: 26
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl)carbonyl or Allyloxy
      carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu(2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)

<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)

<400> SEQUENCE: 25

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr
            20                  25
```

<210> SEQ ID NO 26
<211> LENGTH: 27
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl)carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu(2-Propen-1-yl or allyl)
<220> FEATURE:
<221> NAME/KEY: MOD_RES
<222> LOCATION: (16)..(16)
<223> OTHER INFORMATION: Asp(tert-Butoxy)

<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)

<400> SEQUENCE: 26

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr Gly
            20                  25
```

<210> SEQ ID NO 27
<211> LENGTH: 28
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
      carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu(2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)
<220> FEATURE:
<221> NAME/KEY: MOD_RES
<222> LOCATION: (28)..(28)
<223> OTHER INFORMATION: Gln(triphenylmethyl)

<400> SEQUENCE: 27

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr Gly Gln
            20                  25
```

<210> SEQ ID NO 28
<211> LENGTH: 29
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)

-continued

<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu(2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)
<220> FEATURE:
<221> NAME/KEY: MOD_RES
<222> LOCATION: (28)..(28)
<223> OTHER INFORMATION: Gln(triphenylmethyl)
<220> FEATURE:
<221> NAME/KEY: MOD_RES
<222> LOCATION: (29)..(29)
<223> OTHER INFORMATION: Aib

<400> SEQUENCE: 28

Cys Thr Asn Met Leu Trp Gln Val Phe Glu Lys Ala Arg Lys Glu Asp
1               5                   10                  15

```
Leu Tyr Lys Ser Tyr Asp Ser Thr Phe Thr Gly Gln Xaa
            20                  25


<210> SEQ ID NO 29
<211> LENGTH: 30
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
      carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu(2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
```

<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)
<220> FEATURE:
<221> NAME/KEY: MOD_RES
<222> LOCATION: (28)..(28)
<223> OTHER INFORMATION: Gln(triphenylmethyl)
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (30)..(30)
<223> OTHER INFORMATION: His(triphenylmethyl)

<400> SEQUENCE: 29

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr Gly Gln Xaa His
            20                  25                  30
```

<210> SEQ ID NO 30
<211> LENGTH: 30
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is  circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (16)..(16)
<223> OTHER INFORMATION: Asp(tert-Butoxy)

<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)
<220> FEATURE:
<221> NAME/KEY: MOD_RES
<222> LOCATION: (28)..(28)
<223> OTHER INFORMATION: Gln(triphenylmethyl)
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (30)..(30)
<223> OTHER INFORMATION: His(triphenylmethyl)

<400> SEQUENCE: 30

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr Gly Gln Xaa His
            20                  25                  30
```

<210> SEQ ID NO 31
<211> LENGTH: 29
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)

<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)
<220> FEATURE:
<221> NAME/KEY: MOD_RES
<222> LOCATION: (28)..(28)
<223> OTHER INFORMATION: Gln(triphenylmethyl)
<220> FEATURE:
<221> NAME/KEY: MOD_RES
<222> LOCATION: (29)..(29)
<223> OTHER INFORMATION: Aib

<400> SEQUENCE: 31

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr Gly Gln Xaa
            20                  25
```

<210> SEQ ID NO 32
<211> LENGTH: 30
<212> TYPE: PRT
<213> ORGANISM: Artificial Sequence
<220> FEATURE:
<223> OTHER INFORMATION: The sequence is artificially synthesized
<220> FEATURE:

-continued

<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (29)..(29)
<223> OTHER INFORMATION: Aib

<400> SEQUENCE: 32

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr Gly Gln Xaa His
            20                  25                  30
```

<210> SEQ ID NO 33
<211> LENGTH: 15
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys( t-butyloxycarbonyl)

<400> SEQUENCE: 33

```
Cys Thr Asn Met Leu Trp Gln Val Phe Glu Lys Ala Arg Lys Glu
1               5                   10                  15
```

<210> SEQ ID NO 34
<211> LENGTH: 16
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)

<400> SEQUENCE: 34

Cys Thr Asn Met Leu Trp Gln Val Phe Glu Lys Ala Arg Lys Glu Asp
1 5 10 15

<210> SEQ ID NO 35
<211> LENGTH: 17
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)

<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)

<400> SEQUENCE: 35

Cys Thr Asn Met Leu Trp Gln Val Phe Glu Lys Ala Arg Lys Glu Asp
1               5                   10                  15

Leu

<210> SEQ ID NO 36
<211> LENGTH: 18
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)

<400> SEQUENCE: 36

Cys Thr Asn Met Leu Trp Gln Val Phe Glu Lys Ala Arg Lys Glu Asp
1               5                   10                  15

Leu Tyr

<210> SEQ ID NO 37
<211> LENGTH: 19
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)

<400> SEQUENCE: 37

```
Cys Thr Asn Met Leu Trp Gln Val Phe Glu Lys Ala Arg Lys Glu Asp
1               5                   10                  15

Leu Tyr Lys
```

<210> SEQ ID NO 38
<211> LENGTH: 20
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:

<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)
<220> FEATURE:
<221> NAME/KEY: MOD_RES
<222> LOCATION: (20)..(20)
<223> OTHER INFORMATION: Ser(tert-butyl)

<400> SEQUENCE: 38

```
Cys Thr Asn Met Leu Trp Gln Val Phe Glu Lys Ala Arg Lys Glu Asp
1               5                   10                  15

Leu Tyr Lys Ser
            20
```

<210> SEQ ID NO 39
<211> LENGTH: 21
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)

<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)

<400> SEQUENCE: 39

```
Cys Thr Asn Met Leu Trp Gln Val Phe Glu Lys Ala Arg Lys Glu Asp
1               5                   10                  15

Leu Tyr Lys Ser Tyr
            20
```

<210> SEQ ID NO 40
<211> LENGTH: 22
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:

<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)

<400> SEQUENCE: 40

```
Cys Thr Asn Met Leu Trp Gln Val Phe Glu Lys Ala Arg Lys Glu Asp
1               5                   10                  15

Leu Tyr Lys Ser Tyr Asp
            20
```

<210> SEQ ID NO 41
<211> LENGTH: 23
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)

<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)

<400> SEQUENCE: 41

```
Cys Thr Asn Met Leu Trp Gln Val Phe Glu Lys Ala Arg Lys Glu Asp
1               5                   10                  15

Leu Tyr Lys Ser Tyr Asp Ser
            20
```

<210> SEQ ID NO 42
<211> LENGTH: 24
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:

```
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
      sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)

<400> SEQUENCE: 42

Cys Thr Asn Met Leu Trp Gln Val Phe Glu Lys Ala Arg Lys Glu Asp
1               5                   10                  15

Leu Tyr Lys Ser Tyr Asp Ser Thr
            20


<210> SEQ ID NO 43
<211> LENGTH: 25
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
```

<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)

<400> SEQUENCE: 43

```
Cys Thr Asn Met Leu Trp Gln Val Phe Glu Lys Ala Arg Lys Glu Asp
1               5                   10                  15

Leu Tyr Lys Ser Tyr Asp Ser Thr Phe
            20                  25
```

<210> SEQ ID NO 44
<211> LENGTH: 26
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:

-continued

<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)

<400> SEQUENCE: 44

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr
            20                  25
```

<210> SEQ ID NO 45
<211> LENGTH: 27
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)

<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp(t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys(t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys(t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)

<400> SEQUENCE: 45

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr Gly
            20                  25
```

<210> SEQ ID NO 46
<211> LENGTH: 28
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp( t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MISC_FEATURE
<222> LOCATION: (11)..(15)
<223> OTHER INFORMATION: Peptide is circular
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)

<223> OTHER INFORMATION: Thr(tert-butyl)
<220> FEATURE:
<221> NAME/KEY: MOD_RES
<222> LOCATION: (28)..(28)
<223> OTHER INFORMATION: Gln(triphenylmethyl)

<400> SEQUENCE: 46

Cys Thr Asn Met Leu Trp Gln Val Phe Glu Lys Ala Arg Lys Glu Asp
1 5 10 15

Leu Tyr Lys Ser Tyr Asp Ser Thr Phe Thr Gly Gln
20 25

<210> SEQ ID NO 47
<211> LENGTH: 21
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp( t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)

<400> SEQUENCE: 47

Cys Thr Asn Met Leu Trp Gln Val Phe Glu Lys Ala Arg Lys Glu Asp
1 5 10 15

Leu Tyr Lys Ser Tyr
20

<210> SEQ ID NO 48
<211> LENGTH: 26
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Cys(triphenylmethyl)
<220> FEATURE:
<221> NAME/KEY: MOD_RES
<222> LOCATION: (2)..(2)
<223> OTHER INFORMATION: Thr(tert-butyl)
<220> FEATURE:
<221> NAME/KEY: MOD_RES
<222> LOCATION: (3)..(3)
<223> OTHER INFORMATION: Asn(triphenylmethyl)
<220> FEATURE:
<221> NAME/KEY: MOD_RES
<222> LOCATION: (6)..(6)
<223> OTHER INFORMATION: Trp( t-butyloxycarbonyl)
<220> FEATURE:
<221> NAME/KEY: MOD_RES
<222> LOCATION: (7)..(7)
<223> OTHER INFORMATION: Gln(triphenylmethyl)
<220> FEATURE:
<221> NAME/KEY: MOD_RES
<222> LOCATION: (10)..(10)
<223> OTHER INFORMATION: Glu(tert-Butoxy)
<220> FEATURE:
<221> NAME/KEY: MOD_RES
<222> LOCATION: (11)..(11)
<223> OTHER INFORMATION: Lys((2-Propen-1-yl) carbonyl or Allyloxy
carbonyl)
<220> FEATURE:
<221> NAME/KEY: MOD_RES
<222> LOCATION: (13)..(13)
<223> OTHER INFORMATION: Arg(2,2,4,6,7-pentamethyldihydrobenzofuran-5-
sulfonyl)
<220> FEATURE:
<221> NAME/KEY: MOD_RES
<222> LOCATION: (14)..(14)
<223> OTHER INFORMATION: Lys( t-butyloxycarbonyl)
<220> FEATURE:
<221> NAME/KEY: MOD_RES
<222> LOCATION: (15)..(15)
<223> OTHER INFORMATION: Glu( 2-Propen-1-yl or allyl)
<220> FEATURE:
<221> NAME/KEY: MOD_RES
<222> LOCATION: (16)..(16)
<223> OTHER INFORMATION: Asp(tert-Butoxy)
<220> FEATURE:
<221> NAME/KEY: MOD_RES
<222> LOCATION: (18)..(18)
<223> OTHER INFORMATION: Tyr(tert-butyl)
<220> FEATURE:
<221> NAME/KEY: MOD_RES
<222> LOCATION: (19)..(19)
<223> OTHER INFORMATION: Lys( t-butyloxycarbonyl)
<220> FEATURE:
<221> NAME/KEY: MOD_RES
<222> LOCATION: (20)..(20)
<223> OTHER INFORMATION: Ser(tert-butyl)
<220> FEATURE:
<221> NAME/KEY: MOD_RES
<222> LOCATION: (21)..(21)
<223> OTHER INFORMATION: Tyr(tert-butyl)
<220> FEATURE:
<221> NAME/KEY: MOD_RES
<222> LOCATION: (22)..(22)
<223> OTHER INFORMATION: Asp(tert-Butoxy)
<220> FEATURE:
<221> NAME/KEY: MOD_RES
<222> LOCATION: (23)..(23)
<223> OTHER INFORMATION: Ser(tert-butyl)
<220> FEATURE:
<221> NAME/KEY: MOD_RES
<222> LOCATION: (24)..(24)
<223> OTHER INFORMATION: Thr(tert-butyl)
<220> FEATURE:
<221> NAME/KEY: MOD_RES
<222> LOCATION: (26)..(26)
<223> OTHER INFORMATION: Thr(tert-butyl)

<400> SEQUENCE: 48

```
Cys Thr Asn Met Leu Trp Gln Val Phe Glu Lys Ala Arg Lys Glu Asp
1               5                   10                  15

Leu Tyr Lys Ser Tyr Asp Ser Thr Phe Thr
            20                  25
```

<210> SEQ ID NO 49
<211> LENGTH: 30
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (1)..(3)
<223> OTHER INFORMATION: Xaa can be any amino acid
<220> FEATURE:
<221> NAME/KEY: VARIANT
<222> LOCATION: (7)..(7)
<223> OTHER INFORMATION: Xaa can be any amino acid
<220> FEATURE:
<221> NAME/KEY: VARIANT
<222> LOCATION: (10)..(10)
<223> OTHER INFORMATION: Xaa can be any amino acid
<220> FEATURE:
<221> NAME/KEY: VARIANT
<222> LOCATION: (12)..(21)
<223> OTHER INFORMATION: Xaa can be any amino acid
<220> FEATURE:
<221> NAME/KEY: VARIANT
<222> LOCATION: (23)..(24)
<223> OTHER INFORMATION: Xaa can be any amino acid
<220> FEATURE:
<221> NAME/KEY: VARIANT
<222> LOCATION: (27)..(30)
<223> OTHER INFORMATION: Xaa can be any amino acid

<400> SEQUENCE: 49

```
Xaa Xaa Xaa Gly Thr Phe Xaa Ser Asp Xaa Ser Xaa Xaa Xaa Xaa Xaa
1               5                   10                  15

Xaa Xaa Xaa Xaa Xaa Phe Xaa Xaa Trp Leu Xaa Xaa Xaa Xaa
            20                  25                  30
```